US011206989B2

(12) United States Patent
Nadeau et al.

(10) Patent No.: US 11,206,989 B2
(45) Date of Patent: Dec. 28, 2021

(54) LIGHT FIELD MANAGEMENT IN AN OPTICAL BIOLOGICAL PARAMETER SENSOR

(71) Applicant: Fitbit, Inc., San Francisco, CA (US)

(72) Inventors: Kyle P. Nadeau, San Francisco, CA (US); Chris H. Sarantos, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 296 days.

(21) Appl. No.: 15/370,303

(22) Filed: Dec. 6, 2016

(65) Prior Publication Data

US 2017/0164848 A1 Jun. 15, 2017

Related U.S. Application Data

(60) Provisional application No. 62/265,793, filed on Dec. 10, 2015.

(51) Int. Cl.
| | | |
|---|---|---|
| *A61B 5/024* | (2006.01) |
| *A61B 5/00* | (2006.01) |
| *A61B 5/08* | (2006.01) |
| *A61B 5/083* | (2006.01) |
| *A61B 5/1455* | (2006.01) |
| *A61B 8/12* | (2006.01) |
| *G02B 3/08* | (2006.01) |
| *G02B 27/42* | (2006.01) |

(52) U.S. Cl.
CPC ........ *A61B 5/02427* (2013.01); *A61B 5/0008* (2013.01); *A61B 5/02416* (2013.01); *A61B 5/02438* (2013.01); *A61B 5/08* (2013.01); *A61B 5/083* (2013.01); *A61B 5/14552* (2013.01); *A61B 5/4875* (2013.01); *A61B 5/0084* (2013.01); *A61B 8/12* (2013.01); *A61B 2562/0242* (2013.01); *A61B 2562/04* (2013.01); *G02B 3/08* (2013.01); *G02B 27/425* (2013.01)

(58) Field of Classification Search
CPC .................................................. A61B 5/02427
See application file for complete search history.

(56) References Cited

U.S. PATENT DOCUMENTS

| 4,367,752 A | 1/1983 | Jimenez et al. |
| 4,771,792 A | 9/1988 | Seale |

(Continued)

FOREIGN PATENT DOCUMENTS

| AU | 2015101168 A4 | 10/2015 |
| CN | 1623175 A | 6/2005 |

(Continued)

OTHER PUBLICATIONS

U.S. Office Action, dated Aug. 4, 2014, issued in U.S. Appl. No. 13/924,784.

(Continued)

*Primary Examiner* — Rochelle D Turchen
(74) *Attorney, Agent, or Firm* — Dority & Manning, P.A.

(57) ABSTRACT

Structures and techniques are provided for shaping or steering a light field for an optical biological parameter sensor such that the light is partially or wholly collimated and enters a person's skin at an oblique angle to the person's skin such that the light has a direction component oriented towards or away from a photodetector of the optical biological parameter sensor.

25 Claims, 14 Drawing Sheets

(56) References Cited

U.S. PATENT DOCUMENTS

| | | |
|---|---|---|
| 4,781,195 A | 11/1988 | Martin |
| 4,846,183 A | 7/1989 | Martin |
| 5,036,856 A | 8/1991 | Thornton |
| 5,101,831 A | 4/1992 | Koyama et al. |
| 5,301,154 A | 4/1994 | Suga |
| 5,318,597 A | 6/1994 | Hauck et al. |
| 5,490,523 A | 2/1996 | Isaacson et al. |
| 5,513,649 A | 5/1996 | Gevins et al. |
| 5,734,625 A | 3/1998 | Kondo |
| 5,738,104 A | 4/1998 | Lo et al. |
| 5,830,137 A | 11/1998 | Scharf |
| 5,954,644 A | 9/1999 | Dettling et al. |
| 6,076,015 A | 6/2000 | Hartley et al. |
| 6,099,478 A | 8/2000 | Aoshima et al. |
| 6,131,076 A | 10/2000 | Stephan et al. |
| 6,241,684 B1 | 6/2001 | Amano et al. |
| 6,289,230 B1 | 9/2001 | Chaiken et al. |
| 6,307,576 B1 | 10/2001 | Rosenfeld |
| 6,360,113 B1 | 3/2002 | Dettling |
| 6,402,690 B1 | 6/2002 | Rhee et al. |
| 6,418,394 B1 | 7/2002 | Puolakanaho et al. |
| 6,583,369 B2 | 6/2003 | Montagnino et al. |
| 6,585,622 B1 | 7/2003 | Shum et al. |
| 6,731,967 B1 | 5/2004 | Turcott |
| 6,882,955 B1 | 4/2005 | Ohlenbusch et al. |
| 6,959,259 B2 | 10/2005 | Vock et al. |
| 6,997,882 B1 | 2/2006 | Parker et al. |
| 7,020,508 B2 | 3/2006 | Stivoric et al. |
| 7,153,262 B2 | 12/2006 | Stivoric et al. |
| 7,171,331 B2 | 1/2007 | Vock et al. |
| 7,252,639 B2 | 8/2007 | Kimura et al. |
| 7,285,090 B2 | 10/2007 | Stivoric et al. |
| 7,334,472 B2 | 2/2008 | Seo et al. |
| 7,539,532 B2 | 5/2009 | Tran |
| 7,579,946 B2 | 8/2009 | Case, Jr. |
| 7,720,306 B2 | 5/2010 | Gardiner et al. |
| 7,909,768 B1 | 3/2011 | Turcott |
| 7,993,276 B2 | 8/2011 | Nazarian et al. |
| 8,040,758 B1 | 10/2011 | Dickinson |
| 8,073,707 B2 | 12/2011 | Teller et al. |
| 8,109,858 B2 | 2/2012 | Redmann |
| 8,140,143 B2 | 3/2012 | Picard et al. |
| 8,152,745 B2 | 4/2012 | Smith et al. |
| 8,157,731 B2 | 4/2012 | Teller et al. |
| 8,172,761 B1 | 5/2012 | Rulkov et al. |
| 8,199,126 B1 | 6/2012 | Taubman |
| 8,211,503 B2 | 7/2012 | Tsao et al. |
| 8,346,328 B2 | 1/2013 | Mannheimer et al. |
| 8,386,042 B2 | 2/2013 | Yudovsky et al. |
| 8,398,546 B2 | 3/2013 | Pacione et al. |
| 8,444,578 B2 | 5/2013 | Bourget et al. |
| 8,446,275 B2 | 5/2013 | Utter, II |
| 8,475,367 B1 | 7/2013 | Yuen et al. |
| 8,579,827 B1 | 11/2013 | Rulkov et al. |
| 8,641,612 B2 | 2/2014 | Teller et al. |
| 8,742,325 B1 | 6/2014 | Droz et al. |
| 8,792,981 B2 | 7/2014 | Yudovsky et al. |
| 8,868,377 B2 | 10/2014 | Yuen et al. |
| 8,909,543 B2 | 12/2014 | Tropper et al. |
| 8,920,332 B2 | 12/2014 | Hong et al. |
| 8,936,552 B2 | 1/2015 | Kateraas et al. |
| 8,945,017 B2 | 2/2015 | Venkatraman et al. |
| 8,948,832 B2 | 2/2015 | Hong et al. |
| 8,954,135 B2 | 2/2015 | Yuen et al. |
| 8,956,303 B2 | 2/2015 | Hong et al. |
| 8,961,413 B2 | 2/2015 | Teller et al. |
| 8,998,815 B2 | 4/2015 | Venkatraman et al. |
| 9,005,129 B2 | 4/2015 | Venkatraman et al. |
| 9,014,790 B2 | 4/2015 | Richards et al. |
| 9,031,812 B2 | 5/2015 | Roberts et al. |
| 9,042,971 B2 | 5/2015 | Brumback et al. |
| 9,044,149 B2 | 6/2015 | Richards et al. |
| 9,044,150 B2 | 6/2015 | Brumback et al. |
| 9,049,998 B2 | 6/2015 | Brumback et al. |
| 9,089,760 B2 | 7/2015 | Tropper et al. |
| 9,113,794 B2 | 8/2015 | Hong et al. |
| 9,113,795 B2 | 8/2015 | Hong et al. |
| 9,226,663 B2 | 1/2016 | Fei |
| 9,237,855 B2 | 1/2016 | Hong et al. |
| 9,282,902 B2 | 3/2016 | Richards et al. |
| 9,307,917 B2 | 4/2016 | Hong et al. |
| 9,314,166 B1 | 4/2016 | Brady et al. |
| 9,392,946 B1 | 7/2016 | Sarantos et al. |
| 9,402,552 B2 | 8/2016 | Richards et al. |
| 9,456,787 B2 | 10/2016 | Venkatraman et al. |
| 9,662,053 B2 | 5/2017 | Richards et al. |
| 9,775,548 B2 | 10/2017 | Sarantos et al. |
| 2001/0044588 A1 | 11/2001 | Mault |
| 2002/0077536 A1 | 6/2002 | Diab et al. |
| 2002/0091329 A1 | 7/2002 | Heikkila et al. |
| 2002/0139936 A1* | 10/2002 | Dumas ............... G01N 21/6452 250/458.1 |
| 2003/0107487 A1 | 6/2003 | Korman et al. |
| 2003/0163710 A1 | 8/2003 | Ortiz et al. |
| 2003/0229276 A1 | 12/2003 | Sarussi et al. |
| 2004/0171969 A1 | 9/2004 | Socci et al. |
| 2004/0190085 A1 | 9/2004 | Silverbrook et al. |
| 2004/0236227 A1 | 11/2004 | Gueissaz |
| 2005/0020927 A1 | 1/2005 | Blondeau et al. |
| 2005/0054940 A1 | 3/2005 | Almen |
| 2005/0245793 A1 | 11/2005 | Hilton et al. |
| 2005/0253047 A1 | 11/2005 | Maegawa et al. |
| 2006/0052727 A1 | 3/2006 | Palestrant |
| 2006/0195020 A1 | 8/2006 | Martin et al. |
| 2007/0213020 A1 | 9/2007 | Novac |
| 2007/0219059 A1 | 9/2007 | Schwartz et al. |
| 2007/0265533 A1 | 11/2007 | Tran |
| 2008/0039729 A1 | 2/2008 | Cho et al. |
| 2008/0097221 A1 | 4/2008 | Florian |
| 2008/0214360 A1 | 9/2008 | Stirling et al. |
| 2008/0214903 A1 | 9/2008 | Orbach |
| 2009/0012433 A1 | 1/2009 | Fernstrom et al. |
| 2009/0132197 A1 | 5/2009 | Rubin et al. |
| 2009/0143655 A1 | 6/2009 | Shani |
| 2009/0163783 A1 | 6/2009 | Mannheimer et al. |
| 2009/0292332 A1 | 11/2009 | Li et al. |
| 2009/0318779 A1 | 12/2009 | Tran |
| 2010/0026995 A1 | 2/2010 | Merritt et al. |
| 2010/0063365 A1 | 3/2010 | Pisani et al. |
| 2010/0079291 A1 | 4/2010 | Kroll et al. |
| 2010/0106044 A1 | 4/2010 | Linderman |
| 2010/0113948 A1 | 5/2010 | Yang et al. |
| 2010/0152600 A1 | 6/2010 | Droitcour et al. |
| 2010/0204550 A1 | 8/2010 | Heneghan et al. |
| 2010/0249633 A1 | 9/2010 | Droitcour et al. |
| 2010/0274100 A1 | 10/2010 | Behar et al. |
| 2010/0292568 A1 | 11/2010 | Droitcour et al. |
| 2010/0298650 A1 | 11/2010 | Moon et al. |
| 2010/0298651 A1 | 11/2010 | Moon et al. |
| 2010/0298653 A1 | 11/2010 | McCombie et al. |
| 2010/0298661 A1 | 11/2010 | McCombie et al. |
| 2010/0331145 A1 | 12/2010 | Lakovic et al. |
| 2010/0331657 A1 | 12/2010 | Mensinger et al. |
| 2011/0009727 A1 | 1/2011 | Mensinger et al. |
| 2011/0032105 A1 | 2/2011 | Hoffman et al. |
| 2011/0066010 A1 | 3/2011 | Moon et al. |
| 2011/0112442 A1 | 5/2011 | Meger et al. |
| 2011/0118621 A1 | 5/2011 | Chu |
| 2011/0237911 A1 | 9/2011 | Lamego et al. |
| 2011/0237912 A1 | 9/2011 | Couronne et al. |
| 2011/0276304 A1 | 11/2011 | Yin et al. |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0123232 A1 | 5/2012 | Najarian et al. |
| 2012/0140233 A1 | 6/2012 | Rockwell et al. |
| 2012/0143067 A1 | 6/2012 | Watson et al. |
| 2012/0150074 A1 | 6/2012 | Yanev et al. |
| 2012/0172733 A1 | 7/2012 | Park |
| 2012/0226471 A1 | 9/2012 | Yuen et al. |
| 2012/0226472 A1 | 9/2012 | Yuen et al. |

(56) References Cited

U.S. PATENT DOCUMENTS

| | | |
|---|---|---|
| 2012/0232432 A1 | 9/2012 | Kahn et al. |
| 2012/0245439 A1 | 9/2012 | Andre et al. |
| 2012/0253486 A1 | 10/2012 | Niemimaki |
| 2012/0255875 A1 | 10/2012 | Vicente et al. |
| 2012/0271180 A1 | 10/2012 | Ren et al. |
| 2012/0274508 A1 | 11/2012 | Brown et al. |
| 2012/0316471 A1 | 12/2012 | Rahman et al. |
| 2013/0009779 A1 | 1/2013 | Wittling et al. |
| 2013/0053661 A1 | 2/2013 | Alberth et al. |
| 2013/0073254 A1 | 3/2013 | Yuen et al. |
| 2013/0073255 A1 | 3/2013 | Yuen et al. |
| 2013/0077823 A1 | 3/2013 | Mestha et al. |
| 2013/0077826 A1 | 3/2013 | Cowperthwaite et al. |
| 2013/0079607 A1 | 3/2013 | Gareau et al. |
| 2013/0080113 A1 | 3/2013 | Yuen et al. |
| 2013/0106684 A1 | 5/2013 | Weast et al. |
| 2013/0151196 A1 | 6/2013 | Yuen et al. |
| 2013/0158369 A1 | 6/2013 | Yuen et al. |
| 2013/0173171 A1 | 7/2013 | Drysdale et al. |
| 2013/0191034 A1 | 7/2013 | Weast et al. |
| 2013/0211265 A1 | 8/2013 | Bedingham et al. |
| 2013/0218053 A1 | 8/2013 | Kaiser et al. |
| 2013/0245436 A1 | 9/2013 | Tupin, Jr. et al. |
| 2014/0039284 A1 | 2/2014 | Niwayama et al. |
| 2014/0073486 A1 | 3/2014 | Ahmed et al. |
| 2014/0074431 A1 | 3/2014 | Modi |
| 2014/0099614 A1 | 4/2014 | Hu et al. |
| 2014/0107493 A1 | 4/2014 | Yuen et al. |
| 2014/0135612 A1* | 5/2014 | Yuen .................. A61B 5/02405 600/407 |
| 2014/0135631 A1 | 5/2014 | Brumback et al. |
| 2014/0142403 A1 | 5/2014 | Brumback et al. |
| 2014/0228649 A1 | 8/2014 | Rayner |
| 2014/0241626 A1 | 8/2014 | Sull et al. |
| 2014/0275821 A1 | 9/2014 | Beckman |
| 2014/0275852 A1 | 9/2014 | Hong et al. |
| 2014/0275854 A1 | 9/2014 | Venkatraman et al. |
| 2014/0276119 A1 | 9/2014 | Venkatraman et al. |
| 2014/0278139 A1 | 9/2014 | Hong et al. |
| 2014/0288390 A1 | 9/2014 | Hong et al. |
| 2014/0288391 A1 | 9/2014 | Hong et al. |
| 2014/0288392 A1 | 9/2014 | Hong et al. |
| 2014/0288435 A1 | 9/2014 | Richards et al. |
| 2014/0288436 A1 | 9/2014 | Venkatraman et al. |
| 2014/0288438 A1 | 9/2014 | Venkatraman et al. |
| 2014/0303523 A1 | 10/2014 | Hong et al. |
| 2014/0378786 A1 | 12/2014 | Hong et al. |
| 2014/0378787 A1 | 12/2014 | Brumback et al. |
| 2014/0378844 A1 | 12/2014 | Fei |
| 2014/0378872 A1 | 12/2014 | Hong et al. |
| 2015/0025393 A1 | 1/2015 | Hong et al. |
| 2015/0025394 A1 | 1/2015 | Hong et al. |
| 2015/0173631 A1 | 6/2015 | Richards et al. |
| 2015/0196256 A1 | 7/2015 | Venkatraman et al. |
| 2015/0201853 A1 | 7/2015 | Hong et al. |
| 2015/0201854 A1 | 7/2015 | Hong et al. |
| 2015/0223708 A1 | 8/2015 | Richards et al. |
| 2015/0230743 A1 | 8/2015 | Silveira et al. |
| 2015/0230761 A1 | 8/2015 | Brumback et al. |
| 2015/0260573 A1 | 9/2015 | Ishimaru |
| 2015/0282713 A1 | 10/2015 | Fei |
| 2015/0366469 A1 | 12/2015 | Harris et al. |
| 2016/0034634 A9 | 2/2016 | Hong et al. |
| 2016/0058309 A1* | 3/2016 | Han .................. A61B 5/02427 600/479 |
| 2016/0058312 A1* | 3/2016 | Han ...................... G01N 21/55 600/473 |
| 2016/0183818 A1 | 6/2016 | Richards et al. |
| 2016/0302706 A1 | 10/2016 | Richards et al. |
| 2016/0345881 A1 | 12/2016 | Sarantos et al. |
| 2017/0020659 A1* | 1/2017 | Hyde .................. A61B 5/0031 |
| 2017/0027523 A1 | 2/2017 | Venkatraman et al. |

FOREIGN PATENT DOCUMENTS

| | | |
|---|---|---|
| CN | 1729933 | 8/2006 |
| CN | 100362963 C | 1/2008 |
| CN | 101426419 A | 5/2009 |
| CN | 101615098 A | 12/2009 |
| CN | 101730503 | 6/2010 |
| CN | 101742981 A | 6/2010 |
| CN | 102008811 A | 4/2011 |
| CN | 202069586 U | 12/2011 |
| CN | 102389313 A | 3/2012 |
| CN | 102419314 A | 4/2012 |
| CN | 102551686 A | 7/2012 |
| CN | 102750015 A | 10/2012 |
| CN | 102781310 A | 11/2012 |
| CN | 103093420 A | 5/2013 |
| CN | 204520654 U | 8/2015 |
| EP | 1 297 784 A1 | 4/2003 |
| EP | 1 586 353 A1 | 10/2005 |
| EP | 1 721 237 | 8/2012 |
| WO | WO 2014/091424 A2 | 6/2014 |
| WO | WO 2014/091424 A3 | 6/2014 |

OTHER PUBLICATIONS

U.S. Notice of Allowance, dated Nov. 19, 2014, issued in U.S. Appl. No. 13/924,784.
U.S. Office Action, dated Oct. 22, 2014, issued in U.S. Appl. No. 14/290,884.
U.S. Notice of Allowance, dated Feb. 6, 2015, issued in U.S. Appl. No. 14/290,884.
U.S. Office Action, dated Jun. 22, 2015, issued in U.S. Appl. No. 14/693,710.
U.S. Notice of Allowance, dated Jul. 27, 2015, issued in U.S. Appl. No. 14/693,710.
U.S. Notice of Allowance, dated Apr. 15, 2016, issued in U.S. Appl. No. 14/954,753.
U.S. Office Action, dated Oct. 26, 2016, issued in U.S. Appl. No. 15/195,911.
U.S. Notice of Allowance, dated Jan. 23, 2017, issued in U.S. Appl. No. 15/195,911.
U.S. Notice of Allowance, dated Sep. 23, 2014, issued in U.S. Appl. No. 14/292,669.
U.S. Notice of Allowance (Corrected Notice of Allowability), dated Oct. 14, 2014, issued in U.S. Appl. No. 14/292,669.
U.S. Notice of Allowance (Corrected Notice of Allowability), dated Dec. 31, 2014, issued in U.S. Appl. No. 14/292,669.
U.S. Notice of Allowance, dated Oct. 14, 2014, issued in U.S. Appl. No. 14/295,144.
U.S. Notice of Allowance, dated Dec. 3, 2014, issued in U.S. Appl. No. 14/295,144.
U.S. Notice of Allowance, dated Sep. 26, 2014, issued in U.S. Appl. No. 14/295,158.
U.S. Notice of Allowance (Corrected Notice of Allowability), dated Dec. 31, 2014, issued in U.S. Appl. No. 14/295,158.
U.S. Office Action, dated Jan. 23, 2015, issued in U.S. Appl. No. 14/507,184.
U.S. Final Office Action, dated May 11, 2015, issued in U.S. Appl. No. 14/507,184.
U.S. Notice of Allowance, dated Aug. 11, 2015, issued in U.S. Appl. No. 14/507,184.
U.S. Notice of Allowance (Corrected Notice of Allowability), dated Dec. 18, 2015, issued in U.S. Appl. No. 14/507,184.
U.S. Office Action, dated Jan. 26, 2015, issued in U.S. Appl. No. 14/295,161.
U.S. Notice of Allowance, dated Apr. 14, 2015, issued in U.S. Appl. No. 14/295,161.
U.S. Notice of Allowance, dated Jul. 28, 2015, issued in U.S. Appl. No. 14/295,161.
U.S. Office Action, dated May 11, 2015, issued in U.S. Appl. No. 14/673,630.
U.S. Notice of Allowance, dated Nov. 25, 2015, issued in U.S. Appl. No. 14/673,630.

(56) References Cited

OTHER PUBLICATIONS

U.S. Notice of Allowance (Corrected Notice of Allowability), dated Mar. 21, 2016, issued in U.S. Appl. No. 14/673,630.
U.S. Office Action, dated Jan. 27, 2015, issued in U.S. Appl. No. 14/507,173.
U.S. Notice of Allowance, dated Apr. 17, 2015, issued in U.S. Appl. No. 14/507,173.
U.S. Notice of Allowance (Corrected Notice of Allowability), dated Jul. 16, 2015, issued in U.S. Appl. No. 14/507,173.
U.S. Office Action, dated Jun. 8, 2015, issued in U.S. Appl. No. 14/673,634.
U.S. Final Office Action, dated Nov. 4, 2015, issued in U.S. Appl. No. 14/673,634.
U.S. Office Action, dated Jul. 13, 2016, issued in U.S. Appl. No. 14/673,634.
U.S. Office Action, dated Feb. 9, 2017, issued in U.S. Appl. No. 14/673,634.
U.S. Office Action, dated Aug. 5, 2014, issued in U.S. Appl. No. 14/292,673.
U.S. Notice of Allowance, dated Dec. 8, 2014, issued in U.S. Appl. No. 14/292,673.
U.S. Notice of Allowance (Corrected Notice of Allowability), dated Mar. 5, 2015, issued in U.S. Appl. No. 14/292,673.
U.S. Office Action, dated Sep. 18, 2014, issued in U.S. Appl. No. 14/295,059.
U.S. Notice of Allowance, dated Jan. 28, 2015, issued in U.S. Appl. No. 14/295,059.
U.S. Notice of Allowance (Corrected Notice of Allowability), dated Mar. 11, 2015, issued in U.S. Appl. No. 14/295,059.
U.S. Office Action, dated Dec. 24, 2014, issued in U.S. Appl. No. 14/295,076.
U.S. Final Office Action, dated Apr. 15, 2015, issued in U.S. Appl. No. 14/295,076.
U.S. Office Action, dated Oct. 22, 2015, issued in U.S. Appl. No. 14/295,076.
U.S. Notice of Allowance, dated May 24, 2016, issued in U.S. Appl. No. 14/295,076.
U.S. Office Action, dated Jul. 31, 2014, issued in U.S. Appl. No. 14/295,122.
U.S. Notice of Allowance, dated Nov. 24, 2014, issued in U.S. Appl. No. 14/295,122.
U.S. Notice of Allowance (Corrected Notice of Allowability), dated Jan. 5, 2015, issued in U.S. Appl. No. 14/295,122.
U.S. Office Action dated Dec. 22, 2016, issued in U.S. Appl. No. 14/599,039.
U.S. Office Action, dated Mar. 14, 2014, issued in U.S. Appl. No. 14/154,009.
U.S. Office Action, dated Sep. 29, 2014, issued in U.S. Appl. No. 14/154,009.
U.S. Notice of Allowance, dated Jan. 21, 2015, issued in U.S. Appl. No. 14/154,009.
U.S. Office Action, dated Nov. 25, 2014, issued in U.S. Appl. No. 14/154,019.
U.S. Notice of Allowance, dated Mar. 20, 2015, issued in U.S. Appl. No. 14/154,019.
U.S. Notice of Allowance (Corrected Notice of Allowability), dated May 14, 2015, issued in U.S. Appl. No. 14/154,019.
U.S. Office Action, dated Dec. 10, 2014, issued in U.S. Appl. No. 14/484,104.
U.S. Notice of Allowance, dated Mar. 19, 2015, issued in U.S. Appl. No. 14/484,104.
U.S. Notice of Allowance (Corrected Notice of Allowability), dated May 6, 2015, issued in U.S. Appl. No. 14/484,104.
U.S. Office Action, dated Dec. 4, 2014, issued in U.S. Appl. No. 14/216,743.
U.S. Final Office Action, dated Apr. 8, 2015, issued in U.S. Appl. No. 14/216,743.
U.S. Office Action, dated Oct. 2, 2015, issued in U.S. Appl. No. 14/216,743.
U.S. Final Office Action, dated Feb. 8, 2016, issued in U.S. Appl. No. 14/216,743.
U.S. Office Action, dated May 16, 2016, issued in U.S. Appl. No. 14/216,743.
U.S. Office Action, dated Jan. 13, 2017, issued in U.S. Appl. No. 14/216,743.
U.S. Office Action, dated Mar. 12, 2015, issued in U.S. Appl. No. 14/481,020.
U.S. Final Office Action, dated Jul. 7, 2015, issued in U.S. Appl. No. 14/481,020.
U.S. Office Action, dated Oct. 27, 2015, issued in U.S. Appl. No. 14/481,020.
U.S. Final Office Action, dated May 13, 2016, issued in U.S. Appl. No. 14/481,020.
U.S. Examiner's Answer to Appeal Brief, dated Jan. 23, 2017, issued in U.S. Appl. No. 14/481,020.
U.S. Office Action, dated Aug. 22, 2014, issued in U.S. Appl. No. 14/250,256.
U.S. Final Office Action, dated Nov. 21, 2014, issued in U.S. Appl. No. 14/250,256.
U.S. Office Action, dated Jul. 8, 2015, issued in U.S. Appl. No. 14/250,256.
U.S. Final Office Action, dated Oct. 23, 2015, issued in U.S. Appl. No. 14/250,256.
U.S. Office Action, dated Mar. 17, 2016, issued in U.S. Appl. No. 14/250,256.
U.S. Final Office Action, dated Jun. 29, 2016, issued in U.S. Appl. No. 14/250,256.
U.S. Office Action, dated Jan. 9, 2017, issued in U.S. Appl. No. 14/250,256.
U.S. Office Action, dated Oct. 7, 2014, issued in U.S. Appl. No. 14/481,762.
U.S. Final Office Action, dated Dec. 19, 2014, issued in U.S. Appl. No. 14/481,762.
U.S. Office Action, dated Jul. 7, 2015, issued in U.S. Appl. No. 14/481,762.
U.S. Final Office Action, dated Nov. 5, 2015, issued in U.S. Appl. No. 14/481,762.
U.S. Office Action, dated May 11, 2016, issued in U.S. Appl. No. 14/481,762.
U.S. Final Office Action, dated Oct. 19, 2016, issued in U.S. Appl. No. 14/481,762.
U.S. Office Action, dated Apr. 12, 2017, issued in U.S. Appl. No. 14/481,762.
U.S. Office Action, dated Nov. 19, 2015, issued in U.S. Appl. No. 14/724,750.
U.S. Notice of Allowance, dated Mar. 8, 2016, issued in U.S. Appl. No. 14/724,750.
U.S. Office Action dated Sep. 8, 2016, issued in U.S. Appl. No. 15/192,447.
U.S. Final Office Action dated Feb. 7, 2017, issued in U.S. Appl. No. 15/192,447.
U.S. Notice of Allowance dated May 24, 2017, issued in U.S. Appl. No. 15/192,447.
Chinese First Office Action dated Sep. 27, 2016 issued in Application No. CN 201410018701.8.
Chinese First Office Action dated Aug. 7, 2015 issued in Application No. CN 201410243180.6.
Chinese First Office Action dated Sep. 2, 2016 issued in Application No. CN 201510745382.5.
Chinese Second Office Action dated Mar. 22, 2017 issued in Application No. CN 201510745382.5.
Chinese First Office Action dated Aug. 3, 2016 issued in Application No. CN 201410243169.X.
Chinese Second Office Action dated Mar. 27, 2017 issued in Application No. CN 201410243169.X.
Chinese First Office Action dated Sep. 26, 2016 issued in Application No. CN 201410243178.9
Chinese First Office Action dated Mar. 3, 2017 issued in Application No. CN 201610622453.7.
European Extended Search Report dated Oct. 25, 2016 issued in Application No. EP 16 16 8661.3.

(56) References Cited

OTHER PUBLICATIONS

Litigation Document—"Complaint For Patent Infringement," filed Sep. 3, 2015, in U.S. District Court of Delaware (Court Docket No. 1: 15-cv-00775-RGA).
Litigation Document—"Report On the Filing or Determination of an Action Regarding a Patent or Trademark," filed Sep. 3, 2015, in U.S. District Court of Delaware (Court Docket No. 1: 15-cv-00775-RGA).
Litigation Document—"Complaint For Patent Infringement," filed Oct. 29, 2015, in U.S. District Court of Delaware (Court Docket No. 1:15-cv-00990-RGA) [Re: U.S. Pat. Nos. 8,868,377, 8,920,332, and 9,089,760].
Litigation Document—"Report On the Filing or Determination of an Action Regarding a Patent or Trademark," filed Oct. 29, 2015, in U.S. District Court of Delaware (Court Docket No. 1:15-cv-00990-RGA) [Re: U.S. Pat. Nos. 8,868,377, 8,920,332, and 9,089,760].
Litigation Document—"Order No. 24: Initial Determination Granting Respondents' Motion for Summary Determination of Invalidity under 35 U.S.C. § 101 with respect to all Three Asserted Patents and Terminating the Investigation in its Entirety," filed Jul. 19, 2016, in United States International Trade Commission, Washington, D.C. (Investigation No. 337-TA-973) [In the Matter of Certain Wearable Activity Tracking Devices, Systems, and Components Thereof].
Litigation Document—"Respondents' Opposition to Complainant's Petition for Review of the Initial Determination Granting Summary Determination that the Asserted Patents are Directed to Ineligible Subject Matter under 35 U.S.C. § 101," filed Aug. 8, 2016, in United States International Trade Commission, Washington, D.C. (Investigation No. 337-TA-973) (4446833v1/014972) [In the Matter of Certain Wearable Activity Tracking Devices, Systems, and Components Thereof].
Litigation Document—"Declaration of Majid Sarrafzadeh in Support of Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 37-TA-973) [In the Matter of Certain Wearable Activity Tracking Devices, Systems, and Components Thereof] [Exhibit 7].
Litigation Document—"Kiaei Declaration in Support of Complainant's Supplemental Brief Regarding Construction of "Operating the Heart Rate Monitor in a Worn Detection Mode" under 35 U.S.C. § 112(f)," filed Apr. 29, 2016, in United States International Trade Commission, Washington, D.C. (Investigation No. 37-TA-973) [In the Matter of Certain Wearable Activity Tracking Devices, Systems, and Components Thereof] [Exhibit 8].
Litigation Document—"Memorandum in Support of Respondents' Motion for Summary Determination that the Asserted Patents are Directed to Ineligible Subject Matter under 35 U.S.C. § 101," filed May 23, 2016, in United States International Trade Commission, Washington, D.C. (Investigation No. 337-TA-973) (44325007v1/014972) [In the Matter of Certain Wearable Activity Tracking Devices, Systems, and Components Thereof].
Litigation Document—"Grimes Declaration in Support of Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 37-TA-973) [In the Matter of Certain Wearable Activity Tracking Devices, Systems, and Components Thereof] [Exhibit 28].
Litigation Document—"Complainant's Brief in Opposition to Respondents' Motion for Summary Determination that the Asserted Patents are Directed to Ineligible Subject Matter under 35 U.S.C. § 101," filed Jun. 2, 2016, in United States International Trade Commission, Washington, D.C. (Investigation No. 337-TA-973) [In the Matter of Certain Wearable Activity Tracking Devices, Systems, and Components Thereof].
Litigation Document—"Complainant's Petition for Review of the Initial Determination Granting Summary Determination that the Asserted Patents are Directed to Ineligible Subject Matter under 35 U.S.C. § 101," filed Aug. 1, 2016, in United States International Trade Commission, Washington, D.C. (Investigation No. 337-TA-973) [In the Matter of Certain Wearable Activity Tracking Devices, Systems, and Components Thereof].
Litigation Document—"Summary Pursuant to 19 C.F.R. § 210.43(b)(2) of Complainant's Petition for Review of the Initial Determination Granting Summary Determination that the Asserted Patents are Directed to Ineligible Subject Matter under 35 U.S.C. § 101," filed Aug. 1, 2016, in United States International Trade Commission, Washington, D.C. (Investigation No. 337-TA-973) [In the Matter of Certain Wearable Activity Tracking Devices, Systems, and Components Thereof].
Litigation Document—"Notice of Commission Determination to Review an Initial Determination Granting Respondents' Motion for Summary Determination that Certain Asserted Claims are Directed to Ineligible Subject Matter under 35 U.S.C. § 101; and on Review to Remand the Investigation to the Presiding Administrative Law Judge," issued Sep. 7, 2016, in United States International Trade Commission, Washington, D.C. (Investigation No. 337-TA-973) [In the Matter of Certain Wearable Activity Tracking Devices, Systems, and Components Thereof].
U.S. Appl. No. 61/736,310, filed Dec. 12, 2012, William Ahmed et al., entitled "Fitness Monitoring Systems and Methods Based on Continuous Collection of Physiological Data," 61pp [Exhibit 4].
U.S. Appl. No. 61/696,525, filed Sep. 4, 2012, William Ahmed et al., entitled "Fitness Monitoring Systems and Methods Based on Continuous Collection of Physiological Data," 47pp [Exhibit 5].
Gasparrini et al. (2013) "Evaluation and Possible Improvements of the ANT Protocol for Home Heart Monitoring Applications," IEEE, 978-1-4673-2874-6/13, 7pp [Exhibit 6].
"UP3™, The world's most advanced tracker," (Oct. 14, 2015) *Jawbone*, 10pp [Exhibit 12].
"UP4™, A fitness tracker so advanced it pays," (Oct. 14, 2015) *Jawbone*, 12pp [Exhibit 13].
"User's Guide, MIO Drive+ Petite," User's guide and how-to videos available at www.mioglobal.com, 3pp [Exhibit 16].
"Solo 915, Heart Rate + Calorie Monitor," (2009) *Sportline®*, [retrieved on Oct. 15, 2010 at www.sportline.com] 25pp [Exhibit 17].
U.S. Notice of Allowance dated Oct. 14, 2014 issued in U.S. Appl. No. 14/295,144, 5pp [Exhibit 18].
"Health Touch™ Plus User Guide," (2011) *Timex Group USA, Inc.*, 12pp [Exhibit 18].
Czarnul, Pawel (Jun. 6-8, 2013) "Design of a Distributed System using Mobile Devices and Workflow Management for Measurement and Control of a Smart Home and Health," Sopot, Poland, *IEEE*, pp. 184-192, 10pp [Exhibit 19].
Rabinovich, Roberto A., and Louvaris, Zafeiris et al. (Feb. 8, 2013) "Validity of Physical Activity Monitors During Daily Life in Patients With COPD," *ERJ Express, European Respiratory Society*, 28pp [Exhibit 24].
Horvath et al. (2007) "The effect of pedometer position and normal gait asymmetry on step count accuracy," *Appl. Physiol. Nutr. Metab.*, 32:409-415, 8pp [Exhibit 32].
Graser et al. (2007) "Effects of Placement, Attachment, and Weight Classification on Pedometer Accuracy," *Journal of Physical Activity and Health*, 4(4):359-369, 13pp [Exhibit 33].
Vyas et al. (2012) "Machine Learning and Sensor Fusion for Estimating Continuous Energy Expenditure," *AI Magazine*, pp. 55-61, 13pp [Exhibit 42].
"New Lifestyles, NL-800 Activity Monitor, User's guide & record book," (2005), New Lifestyles, Inc., 37pp.
"StepWatch Step Activity Monitor, U.S. Pat. No. 5,485,402," (2001) StepWatch™, *Prosthetics Research Study*, 7pp.
Litigation Document—"Plaintiff's Original Complaint For Patent Infringement," filed Jan. 4, 2016, in U.S. District Court for the Eastern District of North Carolina (Court Docket No. 5:16-cv-00002-FL) [Re: U.S. Pat. Nos. 8,923,941, 8,886,269, 8,929,965 and 8,989,830], 11 pages.

(56) References Cited

OTHER PUBLICATIONS

"Activator is One of the Best Cydia iPhone Hacks | Control your iPhone with Gestures," IPHONE-TIPS-AND-ADVICE.COM, [retrieved on Jul. 9, 2013 at http://www.iphone-tips-and-advice.com/activatior.html], 10 pp.
Chudnow, Alan (Dec. 3, 2012) "Basis Wristband Make Its Debut," *The Wired Self Living in a Wired World*, published in Health [retrieved on Jul. 22, 2013 at http://thewiredself.com/health/basis-wrist-band-make-its-debut/], 3pp.
Cooper, Daniel (Aug. 16, 2013) *Withings Pulse review*, http://www.engadget.com/2013/08/16/withings-pulse-revew/, 8 pages.
DesMarais, Christina (posted on Sep. 3, 2013) "Which New Activity Tracker is Best for You?" *Health and Home, Health & Fitness , Guides & Reviews*, [Retrieved on Sep. 23, 2013 at http://www.techlicious.com/guide/which-new-activity-tracker-is-right-for-you/] 4 pp.
Dunn et al. (2007) "A Novel Ring Shaped Photodiode for Reflectance Pulse Oximetry in Wireless Applications," *IEEE Sensors Conference*, pp. 596-599.
Empson, Rip, (Sep. 22, 2011) "Basis Reveals An Awesome New Affordable Heart and Health Tracker You Can Wear On Your Wrist," [retrieved on Sep. 23, 2013 at http://techcrunch.com/2011/09/22/basis-reveals-an-awesome-new . . . ], 3 pp.
Fitbit User's Manual, Last Updated Oct. 22, 2009, 15 pages.
Forerunner® 201 personal trainer owner's manual, (Feb. 2006) Garmin Ltd., 48 pp.
Forerunner® 301 personal trainer owner's manual, (Feb. 2006) Garmin Ltd., 66 pp.
Forerunner® 50 with ANT+Sport™ wireless technology, Owner's Manual, (Nov. 2007) Garmin Ltd., 44 pp.
Forerunner® 205/305 Owner's Manual, GPS-enabled trainer for runners, (2006-2008), Garmin Ltd., 80 pp.
Forerunner® 405CX Owner's Manual, "GPS-Enabled Sports Watch With Wireless Sync," (Mar. 2009), Garmin Ltd., 56 pp.
Forerunner® 110 Owner's Manual, (2010) "GPS-Enabled Sport Watch," Garmin Ltd., 16 pp.
Forerunner® 210 Owner's Manual, (2010) "GPS-Enabled Sport Watch," Garmin Ltd., 28 pp.
Forerunner® 410 Owner's Manual, (Jul. 2012) "GPS-Enabled Sport Watch With Wireless Sync," Garmin Ltd., 52 pp.
Forerunner® 10 Owner's Manual (Aug. 2012), Garmin Ltd., 10 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 910XT Owner's Manual, (Jan. 2013) Garmin Ltd., 56 pp.
Garmin Swim™ Owner's Manual (Jun. 2012), 12 pp.
Larklife, User Manual, (2012) *Lark Technologies*, 7 pp.
Lark/Larkpro, User Manual, (2012) "What's in the box," *Lark Technologies*, 7 pp.
LIFETRNR, User Manual (2003, specific date unknown), NB new balance®, Implus Footcare, LLC, 3 pages.
Nike+ FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
"Parts of Your Band," (Product Release Date Unknown, downloaded Jul. 22, 2013) Jawbone UP Band, 1 page.
Polar WearLink® + Coded Transmitter 31 Coded Transmitter W.I.N.D. User Manual, Polar® Listen to Your Body, Manufactured by Polar Electro Oy, 11 pages.
Rainmaker, (Jun. 25, 2012, updated Feb. 16, 2013) "Garmin Swim watch In-Depth Review," [retrieved on Sep. 9, 2013 at http://www.dcrainmaker.com/2012/06/garmin-swim-in-depth-review.html, 38 pp.
Rainmaker, (Jul. 25, 2013) "Basis B¹ Watch In-Depth Review," [retrieved on Feb. 4, 2014 at http://www.dcrainmaker.com/2013/07/basis-b1-review.html], 56 pp.
"Withings pulse, Quick Installation Guide" (Jul. 24, 2013) Withings Pulse QIG, v 1.3, withings.com/pulse, 16 pages.
Zijlstra, Wiebren, (2004) "Assessment of spatio-temporal parameters during unconstrained walking," *Eur J Appl Physiol*, 92:39-44.
U.S. Final Office Action, dated Aug. 9, 2017, issued in U.S. Appl. No. 14/673,634.
U.S. Final Office Action dated Aug. 3, 2017, issued in U.S. Appl. No. 14/599,039.
U.S. Examiner's Answer to the Appeal Brief before the Patent Trial and Appeal Board [in response to the appeal brief filed Jul. 11, 2017 appealing from the Office action dated Jan. 9, 2017], dated Aug. 24, 2017, issued in U.S. Appl. No. 14/250,256.
Chinese Second Office Action dated Jun. 13, 2017 issued in Application No. CN 201410018701.8.
Chinese Third Office Action dated Sep. 28, 2017 issued in Application No. CN 201410243169.X.
Chinese Second Office Action dated Jun. 15, 2017 issued in Application No. CN 201410243178.9.
Chinese Second Office Action [no translation] dated Sep. 19, 2017 issued in Application No. CN 201610622453.7.
Chinese First Office Action dated Jul. 13, 2017 issued in Application No. CN 201610621114.7.
U.S. Appl. No. 14/214,655, filed Mar. 14, 2014, Hong et al.
U.S. Appl. No. 15/494,257, filed Apr. 21, 2017, Richards et al.
U.S. Office Action, dated Mar. 27, 2018, issued in U.S. Appl. No. 14/673,634.
U.S. Office Action, dated Jan. 12, 2018, issued in U.S. Appl. No. 15/246,387.
U.S. Examiner's Answer to Appeal Brief before the Patent Trial and Appeal Board [in response to the appeal brief filed Sep. 12, 2017 appealing from the Office action dated Jan. 3, 2017, ], dated Nov. 30, 2017, issued in U.S. Appl. No. 14/216,743.
Chinese First Office Action dated Mar. 22, 2018 issued in Application No. CN 201610284612.7.
Chinese Third Office Action dated Jan. 24, 2018 issued in Application No. CN 201610622453.7.
U.S. Notice of Allowance, dated Aug. 29, 2018, issued in U.S. Appl. No. 15/246,387.
U.S. Office Action, dated Jul. 24, 2018, issued in U.S. Appl. No. 14/696,256.
U.S. Patent Trial and Appeal Board's Decision on Appeal, dated Oct. 9, 2018, issued in U.S. Appl. No. 14/216,743.
U.S. Patent Trial and Appeal Board's Decision on Appeal, dated Sep. 14, 2018, issued in U.S. Appl. No. 14/481,020.
U.S. Notice of Allowance, dated Nov. 29, 2018, issued in U.S. Appl. No. 14/481,020.
U.S. Patent Trial and Appeal Board's Decision on Appeal, dated Oct. 9, 2018, issued in U.S. Appl. No. 14/250,256.
Chinese Second Office Action dated Nov. 6, 2018 issued in Application No. CN 201610284612.7.
Chinese Fourth Office Action dated Jun. 1, 2018 issued in Application No. CN 201610622453.7.
Chinese Second Office Action dated Apr. 9, 2018 issued in Application No. CN 201610621114.7.
Chinese Third Office Action dated Sep. 14, 2018 issued in Application No. CN 201610621114.7.
U.S. Appl. No. 16/057,716, filed Aug. 7, 2018, Hong et al.

* cited by examiner

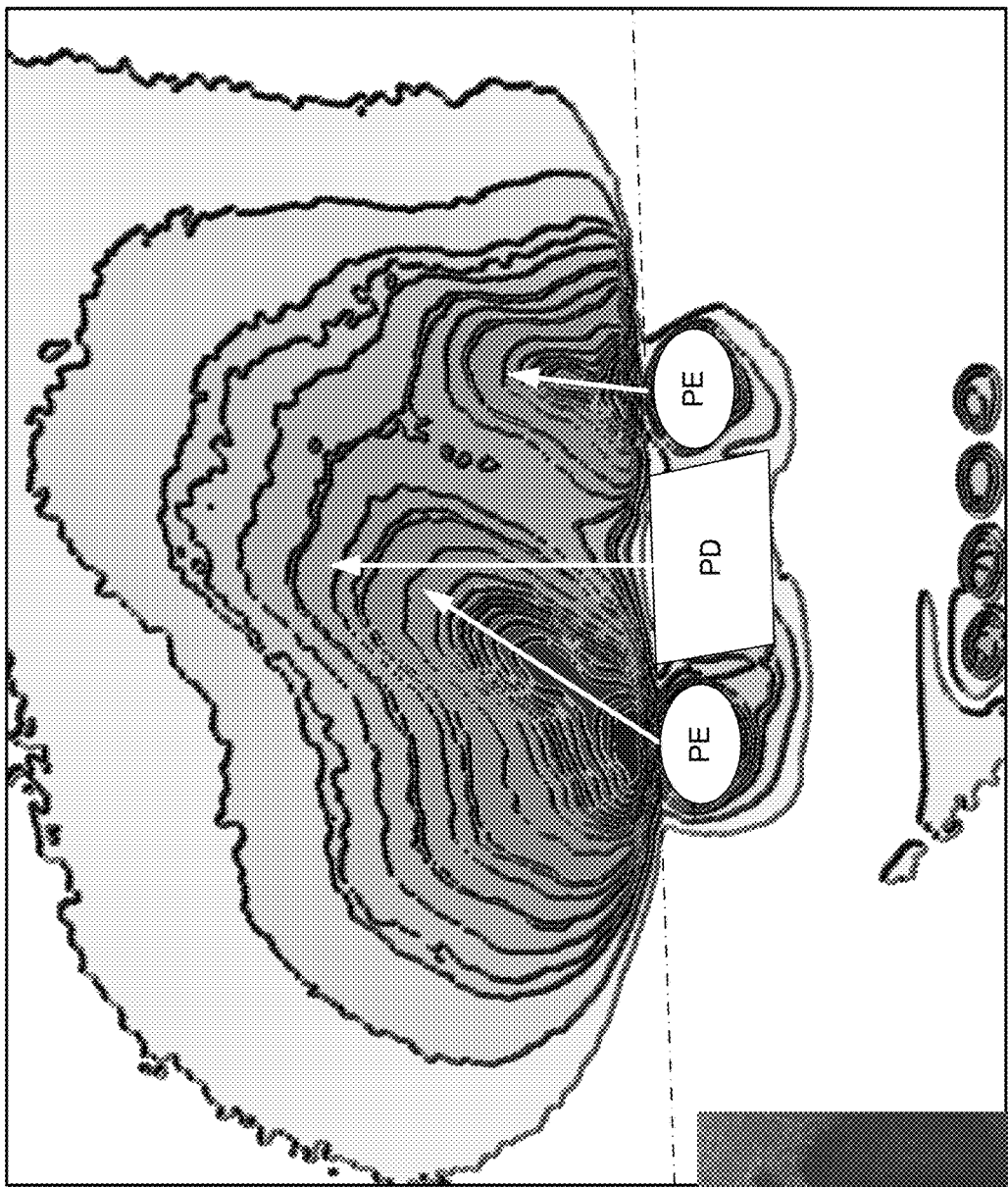
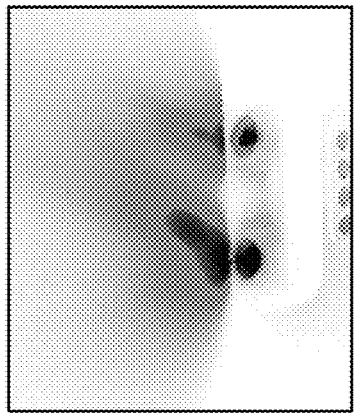
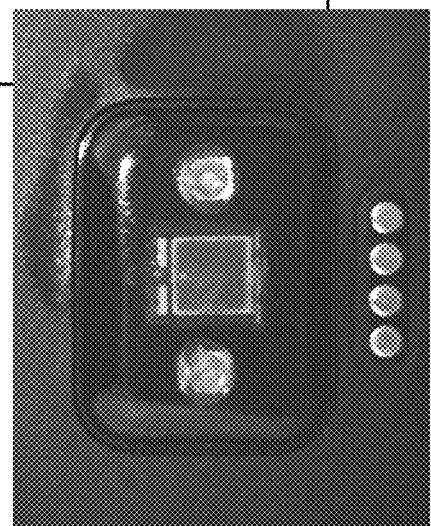
Figure 12'
Figure 12

LIGHT FIELD MANAGEMENT IN AN OPTICAL BIOLOGICAL PARAMETER SENSOR

CROSS REFERENCE TO RELATED APPLICATIONS

This application claims benefit of priority to U.S. Provisional patent application Ser. No. 15/370,303, filed Dec. 6, 2016, and titled "LIGHT FIELD MANAGEMENT IN AN OPTICAL BIOLOGICAL PARAMETER SENSOR."

BACKGROUND

Personal fitness and health monitoring devices, referred to as biometric monitoring devices herein, may include a variety of different sensors that are used to provide feedback regarding various physiological characteristics of a person. Such sensors may include, but are not limited to, optical biological parameter sensors. Optical biological parameter sensors typically operate by illuminating a portion of a person's skin with light from a light source; some of this light is then diffusively reflected back out of the person's skin. By measuring characteristics of the diffusively reflected light, an optical biological parameter sensor may provide data regarding one or more biological parameters.

One common optical biological parameter sensor is a photoplethysmographic (PPG) heart rate sensor. A photoplethysmogram is an optically-obtained measurement of the volume of an organ. In the case of a PPG heart rate sensor, the volume in question is the local volume of blood vessels in the vicinity of the PPG heart rate sensor—as the blood vessels expand and contract with each heartbeat, the volumes of those blood vessels will correspondingly fluctuate. This volumetric fluctuation causes the amount of light that is diffusively reflected out of the person's skin to fluctuate in synchronicity with the person's heart rate. By measuring the intensity of the diffusively reflected light over time, the PPG heart rate sensor may determine the person's heart rate.

Another example of an optical biological parameter sensor is a blood oxygen sensor, which may measure the oxygen saturation of a person's blood by illuminating the person's skin with various wavelengths of light, such as red and infrared light. In the case of red and infrared light, measuring the relative amounts of this red light and infrared light that are absorbed by the person's blood (as reflected in the relative amounts of this light that are diffusively reflected back out of the person's skin) allows the optical biological parameter sensor to determine the amount of oxygen saturation in the person's blood (oxygenated and deoxygenated blood absorb differently depending on the color of the light).

In some instances, a single optical biological parameter sensor may determine multiple biological parameters. For example, a PPG heart rate sensor may not only determine heart rate, but may also determine blood oxygen saturation if properly configured. While optical biological parameter sensors were initially used primarily in hospitals, they are increasingly being used in portable fitness monitoring devices, such as in the FITBIT CHARGE HR™ and the FITBIT SURGE™ wrist-wearable fitness trackers.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some implementations, an apparatus may be provided that includes a collimating light source assembly, one or more first photodetectors, and a first optical light field redirector. The collimating light source assembly may be configured to emit partially or wholly collimated light having a first angular distribution with a first angular centroid defining a first angular direction, and the first optical light field redirector may be positioned so as to receive at least some of the partially or wholly collimated light emitted by the collimating light source assembly. The first optical light field redirector may also be configured to redirect the received partially or wholly collimated light such that the redirected received partially or wholly collimated light has a second angular distribution with a second angular centroid defining a second angular direction having a directional component extending towards the one or more first photodetectors to a greater extent than a corresponding directional component of the first angular direction.

In some such implementations, the apparatus may also include a first light barrier that is interposed between the collimating light source assembly and the one or more first photodetectors.

In some such implementations, the first light barrier may have a first surface facing towards the collimating light source assembly and a second surface facing towards the one or more first photodetectors, and the first surface and the second surface may define a mid-plane between them that is within ±10° of parallel with the first angular direction.

In some other or alternative such implementations, the first light barrier may have a first surface facing towards the collimating light source assembly and a second surface facing towards the one or more first photodetectors, and the first angular direction may be within ±10° of parallel with the average normal vector defined by the first surface and the second surface.

In some additional or alternative such implementations, the apparatus may further include a window with one or more transparent portions. In some such implementations, the first light barrier may interface with the window such that light from the collimating light source assembly does not have a direct optical path from the side of the first light barrier facing towards the collimating light source assembly to the side of the first light barrier facing towards the one or more first photodetectors. Furthermore, one of the one or more transparent portions may extend over the collimating light source assembly and another of the one or more transparent portions may extend over the one or more first photodetectors. In such implementations, the first optical light field redirector may be provided by optical light-turning features molded into the window in the transparent portion extending over the collimating light source assembly.

In some further or alternative such implementations, the intensity of light in the second angular distribution associated with the first angular direction may be less than the intensity of light in the first angular distribution associated with the first angular direction.

In some implementations, the apparatus may further include control logic including a memory and one or more processors. The memory, the one or more processors, the collimating light source assembly, and the one or more first photodetectors may be operably connected, and the memory may store computer-executable instructions for controlling the one or more processors to: cause the collimating light source assembly to emit light, obtain detected light measurements from the one or more first photodetectors in association with the emission of light from the collimating light source assembly, and determine a biological parameter based at least in part on the detected light measurements.

In some such implementations, the memory may further store computer-executable instructions for controlling the one or more processors to obtain a photoplethysmogram from the detected light measurements and determine the biological parameter from the photoplethysmogram.

In some implementations of the apparatus, the biological parameter may be heart rate, blood oxygen saturation (SpO$_2$), respiration rate, blood perfusion, hydration level, tissue oxygen saturation (StO2), tissue metabolic rate, melanin composition, structural orientation of tissue fibers such as muscle and collagen, bulk cell size, bulk cell density, extracellular matrix size, extracellular matrix density, or combinations thereof.

In some implementations of the apparatus, the first angular direction and the second angular direction may form an included angle between them of between 5° and 50°.

In some implementations of the apparatus, the collimating light source assembly may include a light source and a Fresnel lens interposed between the light source and the first optical light field redirector. In such implementations, the Fresnel lens may be configured to partially or wholly collimate light from the light source and to direct the partially or wholly collimated light towards the first optical light field redirector.

In some other implementations of the apparatus, the collimating light source assembly may include one or more light sources and one or more optical reflectors. In such implementations, each optical reflector may have a corresponding light source and the one or more optical reflectors may be configured to reflect light from the corresponding light sources to generate the partially or wholly collimated light having the first angular distribution.

In some other implementations of the apparatus, the collimating light source assembly may include a light source and a diffractive optic interposed between the light source and the first optical light field redirector. In such implementations the diffractive optic may be configured to partially or wholly collimate light from the light source and direct the collimated light towards the first optical light field redirector.

In some implementations of the apparatus, the apparatus may further include a window with one or more transparent portions. One of the one or more transparent portions may extend over the collimating light source assembly, and another of the one or more transparent portions may extend over the one or more first photodetectors. In some such implementations, the first optical light field redirector may be provided by optical light-turning features molded into the window in the transparent portion extending over the collimating light source assembly.

In some implementations of the apparatus, the apparatus may further include one or more optical light field collection optics positioned so as to receive sample-modulated light traveling along a first direction having a component opposite the first angular direction. In such implementations, the received sample-modulated light may have a third angular distribution with a third angular centroid defining a third angular direction, and the one or more optical light field collection optics may be configured to redirect the received sample-modulated light such that the redirected received sample-modulated light has a fourth angular distribution with a fourth angular centroid defining a fourth angular direction that is tilted away from the one or more first photodetectors to a lesser extent than the third angular direction.

In some implementations of the apparatus, the apparatus may further include an optical lens positioned so as to receive sample-modulated light traveling along a first direction having a directional component opposite the first angular direction and having a third angular distribution with a first half-height width. In such implementations, the optical lens may be configured such that the sample-modulated light, after passing through the optical lens, has a fourth angular distribution with a second half-height width that is less than the first half-height width.

In some implementations of the apparatus, the apparatus may further include one or more second photodetectors and a second optical light field redirector positioned so as to receive at least some of the partially or wholly collimated light emitted by the collimating light source assembly. The second optical light field redirector may be configured to redirect the received partially or wholly collimated light such that the redirected received partially or wholly collimated light has a third angular light distribution with a third angular centroid defining a third angular direction having a directional component extending towards the one or more second photodetectors to a greater extent than a corresponding directional component of the first angular direction.

In some such implementations, the apparatus may also include at least one or more additional photodetectors and at least one or more additional optical light field redirectors. In such implementations, the one or more first photodetectors, the one or more second photodetectors, and the at least one or more additional photodetectors may be located within an annular area centered on the collimating light source assembly, and each of the one or more additional optical light field redirectors may be positioned so as to receive at least some of the partially or wholly collimated light emitted by the collimating light source assembly. Each of the one or more additional optical light field redirectors may also be configured to redirect the received partially or wholly collimated light such that the redirected received partially or wholly collimated light has an angular light distribution with an angular centroid defining a an angular direction having a directional component extending towards a corresponding one of the at least one or more additional photodetectors to a greater extent than a corresponding directional component of the first angular direction.

In some such implementations, the apparatus may further include a first light barrier interposed between the collimating light source assembly and the one or more first photodetectors and a second light barrier interposed between the collimating light source assembly and the one or more second photodetectors.

In some implementations, an apparatus may be provided that includes a collimating light source assembly and one or more first photodetectors. The collimating light source assembly may be configured to emit partially or wholly collimated light having a first angular distribution with a first angular centroid defining a first angular direction, and the one or more first photodetectors may define, in aggregate, a substantially planar photosensitive surface. In such implementations, the first angular direction may be at an angle of between 5° and 50° with respect to a normal vector of the substantially planar photosensitive surface and may include a directional component that is directed towards the first photodetector.

In some such implementations, the apparatus may further include a first light barrier interposed between the collimating light source assembly and the one or more first photodetectors.

In some further or alternative such implementations, the collimating light source assembly may be a surface-emitting laser diode that is mounted on a printed circuit and may be configured to emit laser light along a direction normal to the printed circuit with respect to a surface of the printed circuit at a location corresponding with the surface-emitting laser diode, and the printed circuit may be positioned in space relative to the first photodetector such that a major plane of the printed circuit is at an angle of between 5° and 50° with respect to the substantially planar photosensitive surface.

In some further or alternative such implementations of the apparatus, the collimating light source assembly may include one or more light sources and one or more optical reflectors. In such implementations, each optical reflector may have a corresponding light source, and the one or more optical reflectors may be configured to reflect light from the corresponding light sources to generate the partially or wholly collimated light having the first angular distribution.

In some such implementations, the one or more light sources may be arranged in an array that is substantially parallel to the substantially planar photosensitive surface. In some other such implementations, the one or more light sources may be arranged in an array that is within 5° to 50° of parallel with the substantially planar photosensitive surface.

BRIEF DESCRIPTION OF THE DRAWINGS

The various implementations disclosed herein are illustrated by way of example, and not by way of limitation, in the figures of the accompanying drawings, in which like reference numerals refer to similar elements.

FIG. 12 is a picture of an example biometric monitoring device with a PPG sensor having a square photodetector interposed between a left light source equipped with a parabolic reflector and Fresnel lens arrangement as simulated in FIG. 11 and a right light source that does not include such light-steering features.

FIG. 12' is a photograph taken of the example biometric monitoring device of FIG. 12 with the light sources activated while a white projection surface is held perpendicular to the photodetector and generally in-line with the light sources so as to show the beam dispersion patterns produced by each light source.

DETAILED DESCRIPTION

Figure 1:
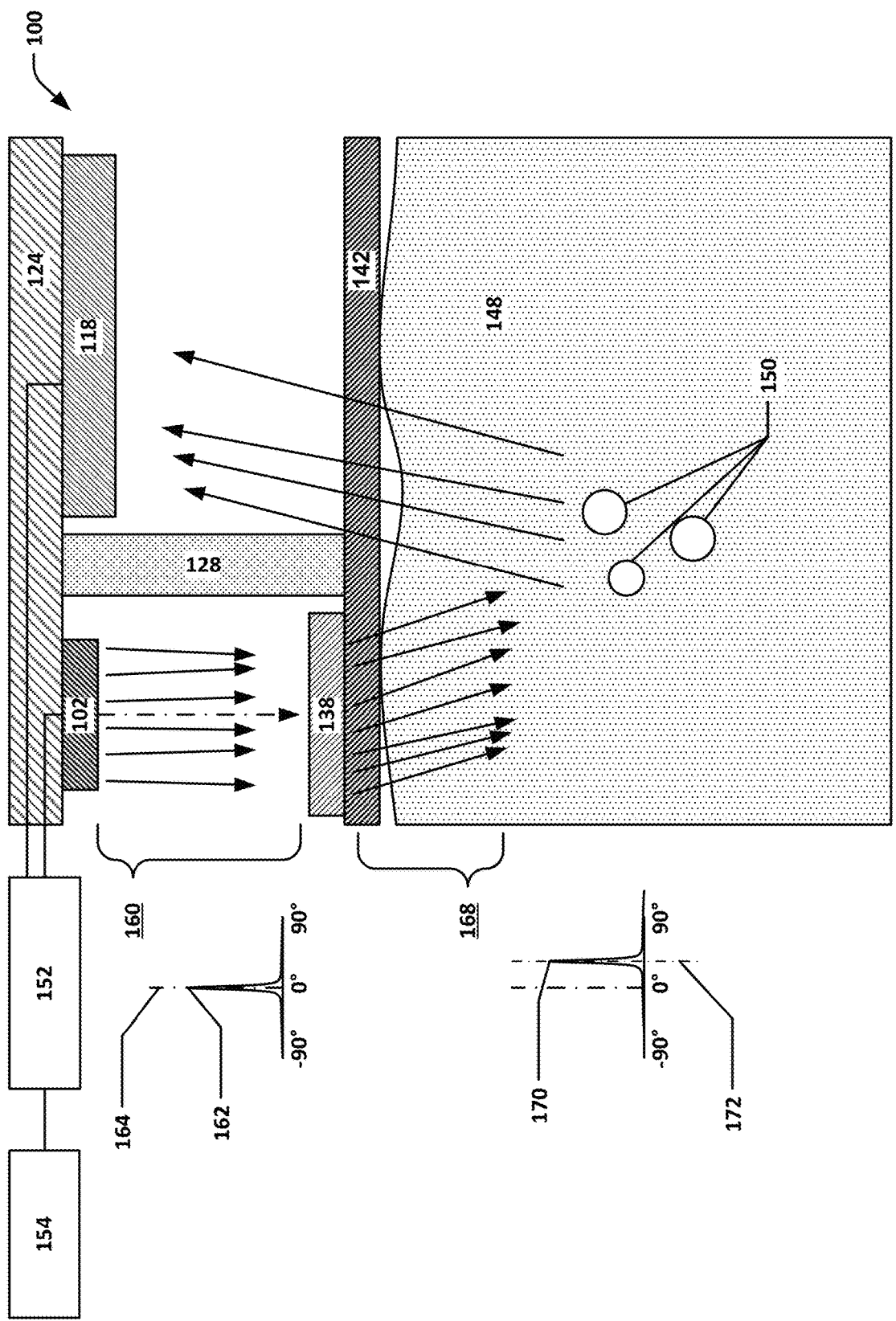
FIG. 1 depicts an example of an optical biological parameter sensor according to the concepts discussed herein.

The present disclosure relates to light-steering or light-shaping optical configurations for an optical biological parameter sensor. Such optical biological parameter sensors may be used in biometric monitoring devices (also referred to herein as "biometric tracking devices," "biometric tracking modules," "wearable fitness monitors," or the like), and may include, but are not limited to, optical biological parameter sensors that measure one or more of heart rate, blood oxygen saturation, peripheral capillary oxygen saturation ($SpO_2$), respiration rate, blood perfusion, hydration level, tissue oxygen saturation ($StO_2$), tissue metabolic rate, melanin composition, structural orientation of tissue fibers such as muscle and collagen, bulk cell size, bulk cell density, extracellular matrix size, and extracellular matrix density.

For example, a person's respiration rate may be evident from a PPG signal in much the same way that a person's heart rate may be reflected in such a signal, e.g., there may be a lower-frequency periodic signal evident in the PPG signal that is indicative of respiratory rate. In another example, a coherent light source, such as a laser, may be used to illuminate a person's skin to produce speckle patterns that may be analyzed in the time and/or spatial domains in order to determine the velocity of scattering particles, i.e., blood cells, in tissue and thereby determine a measure of blood perfusion—such sensors may utilize laser Doppler flowmetry (LDF) and laser speckle imaging (LSI) techniques to obtain such measurements.

In yet another example of an optical biological parameter sensor, infrared light may be emitted into a persons's skin; since water is a strong absorber of infrared light, measuring the amount of attenuation of infrared light may provide a measure of the amount of water in the tissue and thus of the level of hydration of the tissue.

In yet further examples of optical biological parameter sensors, red and infrared light may be used to illuminate a person's skin and the measurements of diffusively reflected light originating therefrom may be used to obtain various oxygenation measurements. For example, the $SpO_2$ level may be measured by comparing the "AC" characteristics of the detected light signals (red and infrared), and the $StO_2$ level may be measured by comparing the "DC" characteristics of such light signals. As noted earlier, the amount of light that is diffusively reflected out of a person's skin varies in time with the person's pulse or heart rate; the time-varying aspect of such a signal is referred to as the "AC" component, and the "constant" portion of such a signal is referred to as the "DC" component. Thus, the DC component may be viewed as the component of the PPG intensity signal that is attributable to light emitted from the background or tissue, whereas the AC component may be viewed as the component of the PPG intensity signal that is attributable to light emitted from pulsatile features, e.g., from changes in blood volume.

In yet another example of an optical biological parameter sensor, melanin composition may be estimated based on the amount of light attenuation that is measured at several different wavelengths. Since melanin absorption of light follows a power-law-like decay as a function of wavelength, it is possible to fit the light attenuation detected at a few wavelengths to an estimate of melanin absorption in order to determine melanin content (since the amount of melanin will govern the amount of absorption).

In a further example, tissue metabolic rate may be related to blood perfusion (oxygen delivery) and the difference in oxygen saturation between arteries and veins, which may be obtained via SpO2 and StO2, respectively. Thus, optical biological parameter sensors that may obtain measurements of these characteristics may be used to also provide an estimate of the tissue metabolic rate.

In yet a further example, light scattering may be determined by taking several measurements as a function of distance from the light source, e.g., such as by positioning multiple photodetectors at varying distances from the light source. By characterizing the light scattering coefficient at multiple wavelengths at these multiple locations, the reduced scattering coefficient vs. wavelength can be fit to a power law model. The amplitude and slope of the resulting curve may correspond to average scattering particle density and size, respectively, and may be used to determine cell/extracellular matrix size and density.

These are but a few of the different types of optical biological parameter sensors that may benefit from the light management concepts discussed herein; these light management concepts may also be applied in other types of optical biological parameter sensor, including sensors not yet developed but sharing the same general characteristics outlined below.

Generally speaking, an optical biological parameter sensor will include at least two components—a light source and a light detector or sensor. The light source of a typical optical biological parameter sensor is a surface-mount light-emitting diode (LED), or one or more pairs of such LEDs. The light detector—also referred to herein as a photodetector—of a typical optical biological parameter sensor is often a single-element photodetector element. The light source and the photodetector are typically located near one another so that light from the light source that is transmitted into a person's skin and diffusively reflected is not completely attenuated by travelling through the person's skin before reaching the photodetector.

Most typical optical biological parameter sensors include an optically opaque barrier of some sort that is interposed between the light source and the photodetector; this barrier limits light from the light source from reaching the photodetector directly, which can saturate the photodetector and affect the accuracy of measurements of the diffusively reflected light from the person's skin. By introducing the barrier in between the light source and the photodetector, light from the light source that reaches the photodetector must first exit the optical biological parameter sensor and then be reflected back into the photodetector by some external object, e.g., through diffusive reflection from the person's skin.

The present inventors have determined that a more efficient optical biological parameter sensor may be realized by shaping and steering the light that is emitted from the light source prior to illuminating a person's skin with the light so as to increase the percentage of the light emitted by the light source that reaches the person's skin. For example, the present inventors determined that the light emitted by a light source used in an optical biometric parameter sensor may be wholly or partially collimated so as to have a narrower angular distribution of light, e.g., a light source that emits 90% of its light within ±20° of a center axis may be collimated such that 90% of the light emitted is within ±3° of the center axis. In perfect collimation, all of the light emitted would be parallel and the angular distribution would collapse to a single angle. In actual practice, however, wholly collimated light, i.e., where all of the light is emitted along parallel directions, is difficult or impossible to achieve, and it is to be understood that "collimated" light, as the term is used herein, is used herein to refer to light that is either wholly collimated or to light that is partially collimated, i.e., where at least 90% of the light energy is emitted along directions within a ±10° range of a reference axis. A collimating light source assembly, as the term is used herein, refers to a light source assembly that emits partially or wholly collimated light. A collimating light source assembly may be a light source that emits wholly or partially collimated light without any optical collimating devices, e.g., such as a laser, or a light source, such as an LED, that emits divergent light that may then be wholly or partially collimated by some type of optical collimator, such as a lens or diffractive grating. In the latter case, the collimating light source assembly may be thought of as including both the light source and the optical collimator.

Light from a light source may have a first angular distribution indicating the amount of light (and thus the intensity of light) that is emitted along each angular direction throughout an angular range, e.g., throughout a ±90° angular range. In many light sources, such as LEDs, a majority of the light emitted from the light source will be emitted along directions at angles close to a center axis of the light source, and the intensity of the emitted light will then gradually fall off with increasing angular distance from that center axis.

The angular distribution of a light source—regardless of whether or not it is a collimating light source assembly—may be thought of as having an angular centroid. The angular centroid represents the angle or direction at which 50% of the area under the angular distribution curve lies to one side of the angular centroid and the other 50% of the area under the angular distribution curve lies to the other side of the angular centroid. Thus, for example, if a light source emits light in an axially symmetric manner, the angular centroid would define a direction that was collinear with the axis of axial symmetry. In many, although not all, cases, the angular centroid of an angular light distribution may define the direction of peak light intensity. It is to be understood, however, that angular distributions may sometimes be multimodal in nature, and the angular centroid in such cases may be along an angular direction other than the angular directions at which such peaks occur.

Partially or wholly collimated light from a collimating light source assembly may have a first angular distribution with a first angular centroid defining a first angular direction. Such partially or wholly collimated light may then be redirected using some form of optical light field redirector such that the redirected partially or wholly collimated light may have a second angular distribution that has a second angular centroid defining a second angular direction. According to various implementations disclosed herein, the second angular direction may have a directional component oriented towards the photodetector that is larger than a corresponding directional component of the first angular direction, i.e., the second angular direction may be tilted towards the photodetector to a greater extent than the first angular direction. The term light field, as used herein, refers to the angles and intensities of light propagation from a light source. For example, a theoretical point light source may emit light having a spherical light field since light is emitted in all directions simultaneously, where as a theoretical collimated light source may emit light having a generally linear or two-dimensional light field since such light is emitted in only one direction. Light fields may be shaped and/or redirected using optical components. For example, a portion of a spherical light field may be shaped into a columnar light field after passing through a lens and being partially or wholly collimated; the lens may, in this case, be viewed as an optical light field redirector.

The present inventors determined that if optical biological parameter sensors are implemented such that there is collimation of the light from the light source followed by, or in combination with, an angular tilt of the resulting wholly or partially collimated light towards the photodetector, such implementations may offer superior performance as compared with conventional optical biological parameter sensor designs. For example, the collimation effect may "reclaim" light that might otherwise have struck opaque surfaces within the optical biological parameter sensor and have been lost. Such reclaimed light may instead be redirected such that it is incident on a person's skin, where it may contribute to the diffusely reflected light from the optical biological parameter sensor that may be measured by the photodetector. The angled tilt to the partially or wholly collimated light may cause the light that is introduced into a person's skin to suffer less attenuation en route to the photodetector as a function of the altered light path through the tissue. As a result, more of the light produced by the light source may ultimately be received by the photodetector through diffusive reflection, which either increases the signal strength associated with a particular power level of the light source or allows the light source to provide a desired level of signal strength using a lower power level as compared with optical biological parameter sensors that do not include such features.

Discussed below are various specific example implementations of optical biological parameter sensors that incorporate these, and related, concepts.

FIG. 1 depicts an example of an optical biological parameter sensor according to the concepts discussed herein. In FIG. 1, an optical biological parameter sensor 100 is depicted; the optical biological parameter sensor 100 includes a collimating light source assembly 102 and a first photodetector 118, as well as a first light barrier 128 that is interposed between the collimating light source assembly 102 and the first photodetector 118.

In the optical biological parameter sensor 100, the first photodetector 118 and the collimating light source assembly 102 are mounted to a substrate 124 and operatively connected with control logic provided by a processor 152 and a memory 154. The control logic may store instructions for controlling the collimating light source assembly 102 to emit wholly or partially collimated light, and for obtaining signals or data from the first photodetector 118 in connection or association with such light emission, e.g., data indicating detected light measurements. The control logic may include computer-executable instructions for calculating or determining a biological parameter based on the characteristics, e.g., timing, intensity, duration, and/or wavelength, of the emitted light and on the data received from the first photodetector 118. In some implementations, the control logic may be configured to obtain a photoplethysmogram from the detected light data obtained from the first photodetector (and additional photodetectors, if used) that is used to determine one or more biological parameters.

It is to be understood that the light sources and photodetectors of any of the implementations discussed herein may be similarly operatively connected with similar control logic or other suitable control elements in order to control the operation of the light source(s) and photodetector(s) and to calculate biological parameters based on data associated with the light source(s) and the photodetector(s), even if such control logic components are not explicitly shown in the remaining Figures.

The collimating light source assembly 102 may emit partially or wholly collimated light that has a first angular distribution 160. The first angular distribution 160 may have a first angular centroid 162 that defines a first angular direction 164. In this example, the first angular direction 164 has been assigned a value of 0°, although this is an arbitrary designation. As can be seen, due to the collimation of the light from the collimating light source assembly 102, the first angular distribution is quite narrow, and most of the light emitted by the collimating light source assembly 102 is emitted along directions falling within about ±10° of the 0° mark. In many implementations of optical biological parameter sensor having light barriers, the first angular direction 164 may be within ±10° of an average normal vector of the sides of the light barrier that face towards the collimating light source assembly 102 and the first photodetector 118. Put another way, the first angular direction 164 may be within ±10° of a mid-plane located between the sides of the light barrier 128 that face towards the collimating light source assembly 102 and the first photodetector 118.

The wholly or partially collimated light emitted by the collimating light source assembly 102 may be received by a first optical light field redirector 138, which may be an optical component that causes most or all of the received wholly or partially collimated light to be redirected such that it has a second angular distribution 168. The second angular distribution 168 may have a second angular centroid 170 that defines a second angular direction 172. The angular frame of reference of the second angular distribution 168 is the same as for the first angular distribution 160. As can be seen, the second angular centroid 170, and thus the second angular direction 172, is shifted to the right of the first angular centroid 162, and thus the first angular direction 164, with respect to this frame of reference by approximately 20°-30°. Thus, the intensity of the light emitted along the first angular direction may decrease after the light has passed through the first optical light field redirector 138.

The redirected received wholly or partially collimated light may, after being redirected by the first optical light field redirector 138, passes through a window 142, which may be an optically transparent barrier that rests against a person's skin when a device having the optical biological parameter sensor 100 is worn by the person. The window 142 may prevent moisture, dirt, oil, or other contaminants from reaching the components of the optical biological parameter sensor 100. The redirected received wholly or partially collimated light may then enter a person's skin and pass into the dermis 148 of the person, where it may encounter blood vessels 150. This redirected received wholly or partially collimated light may diffusively reflect off of the blood vessels 150 as well as off of the surrounding tissue; this diffusive reflection may modulate various characteristics of the diffusively reflected light. A portion of the diffusively reflected light may then exit the dermis 148, pass back through the window 142, and strike the first photodetector 118. The diffusively reflected light that reaches the first photodetector 118 may be referred to as "sample-modulated" light since one or more characteristics of the light have been modulated by virtue of interacting with the person's dermis (and blood vessels therein) or the person's skin (the "sample"). This sample-modulated light may be measured by the first photodetector 118, and this data may be provided to the control logic for use in calculating one or more biological parameters.

Figure 2:
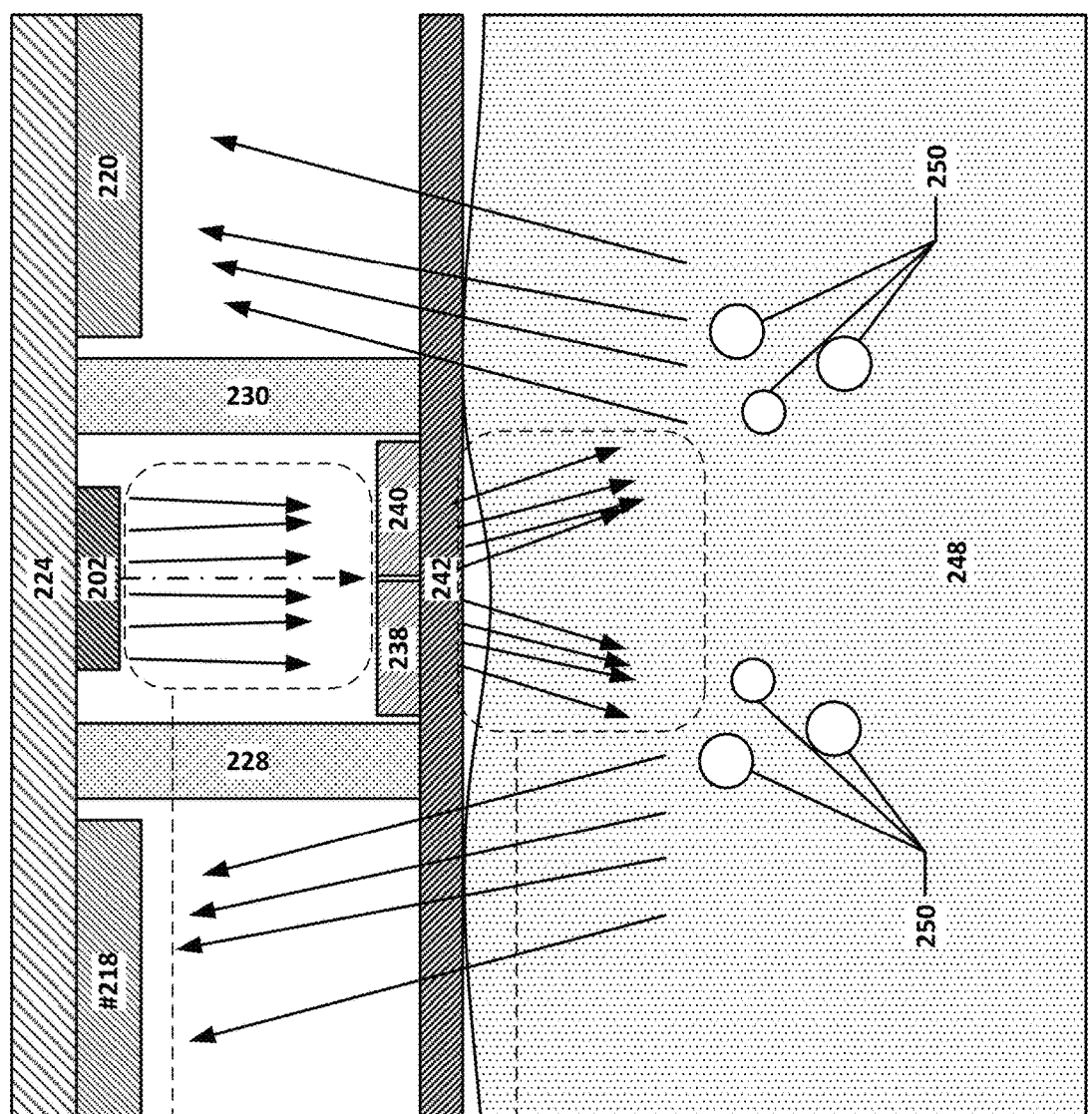
FIG. 2 depicts an example of a dual-photodetector optical biological parameter sensor according to the concepts discussed herein.

In some implementations, multiple photodetectors may be used with a single, common collimating light source assembly. FIG. 2 depicts an example of a dual-photodetector optical biological parameter sensor according to the concepts discussed herein. In FIG. 2, an optical biological parameter sensor 200 is depicted. The optical biological parameter sensor 200 may include a collimating light source assembly 202, a first photodetector 218, and a second photodetector 220 that are mounted to a common substrate 224. A first light barrier 228 may be interposed between the collimating light source assembly 202 and the first photodetector 218; a corresponding second light barrier 230 may be interposed between the collimating light source assembly 202 and the second photodetector 220. The light barriers 228 and 230 may prevent light from the collimating light source assembly 202 from reaching the photodetectors 218 and 220 before first passing through a window 242.

The optical biological parameter sensor 200 also includes a first optical light field redirector 238 and a second optical light field redirector 240; these two optical light field redirectors may be separate components, or may be provided by different regions of a common component. In some cases, these optical light field redirectors may be different portions of the same optical structure, e.g., a ring-shaped optical light field redirector may be centered on the first collimating light source, and a first portion of the ring-shaped optical light field redirector may act as the first optical light field redirector, and a second portion of the ring-shaped optical light field redirector may act as the second optical light field redirector.

Wholly or partially collimated light from the collimating light source assembly 202 may have a first angular distribution 260 that has a first angular centroid 262 that defines a first angular direction 264. As in FIG. 1, the first angular direction 264 has been correlated with a 0° angle with respect to a frame of reference. Due to the collimation provided by the collimating light source assembly 202, the majority of the partially or wholly collimated light may be emitted along directions within a small angular range centered on the first angular direction 264.

The partially or wholly collimated light from the collimating light source assembly 202 that is received by the first optical light field redirector 238 may, as a result of passing through the first optical light field redirector 238, be redirected so as to have a second angular distribution 268 (solid line) with a second angular centroid 270 defining a second angular direction 272. Correspondingly, the partially or wholly collimated light from the collimating light source assembly 202 that is received by the second optical light field redirector 240 may, as a result of passing through the second optical light field redirector 240, be redirected so as to have a third angular distribution 269 (dotted line) with a third angular centroid 274 defining a third angular direction 276. For convenience, the second angular distribution 268 and the third angular distribution 269 are shown with respect to the same frame of reference, i.e., the frame of reference used to show the first angular distribution 260, and in a combined plot.

As can be seen, the second angular direction 272 is oriented towards the first photodetector 218 to a greater extent than the first angular direction 264, i.e., the second angular direction 272 has a directional component in a direction facing towards the first photodetector 218 that is larger in absolute magnitude than the absolute magnitude of a corresponding directional component of the first angular direction 264. Similarly, the third angular direction 276 is also oriented towards the second photodetector 218 to a greater extent than the first angular direction 264, i.e., the third angular direction 272 has a directional component in a direction facing towards the second photodetector 220 that is larger in absolute magnitude than the absolute magnitude of a corresponding directional component of the first angular direction 264. It is to be understood that multiple optical light field redirectors may be employed to produce further angular distributions that may have characteristics similar to those of the second and third angular distributions discussed above.

The redirected received partially or wholly collimated light that is redirected by the first optical light field redirector 238 and the second optical light field redirector 240 may be transmitted through the window 242 and into a person's dermis 248, where it may be diffusively reflected by the dermis 248, the epidermis, and/or blood vessels 250 within the dermis 248. The diffusively reflected light, i.e., sample-modulated light, may then be reflected back out of the dermis and into the first photodetector 218 and the second photodetector 220.

The collimating light source assemblies and the optical light field redirectors discussed above may be provided using any of a variety of different technologies. Various specific implementations are discussed further below, although it is to be understood that the concepts discussed herein are not limited to only these example implementations.

Figure 3:
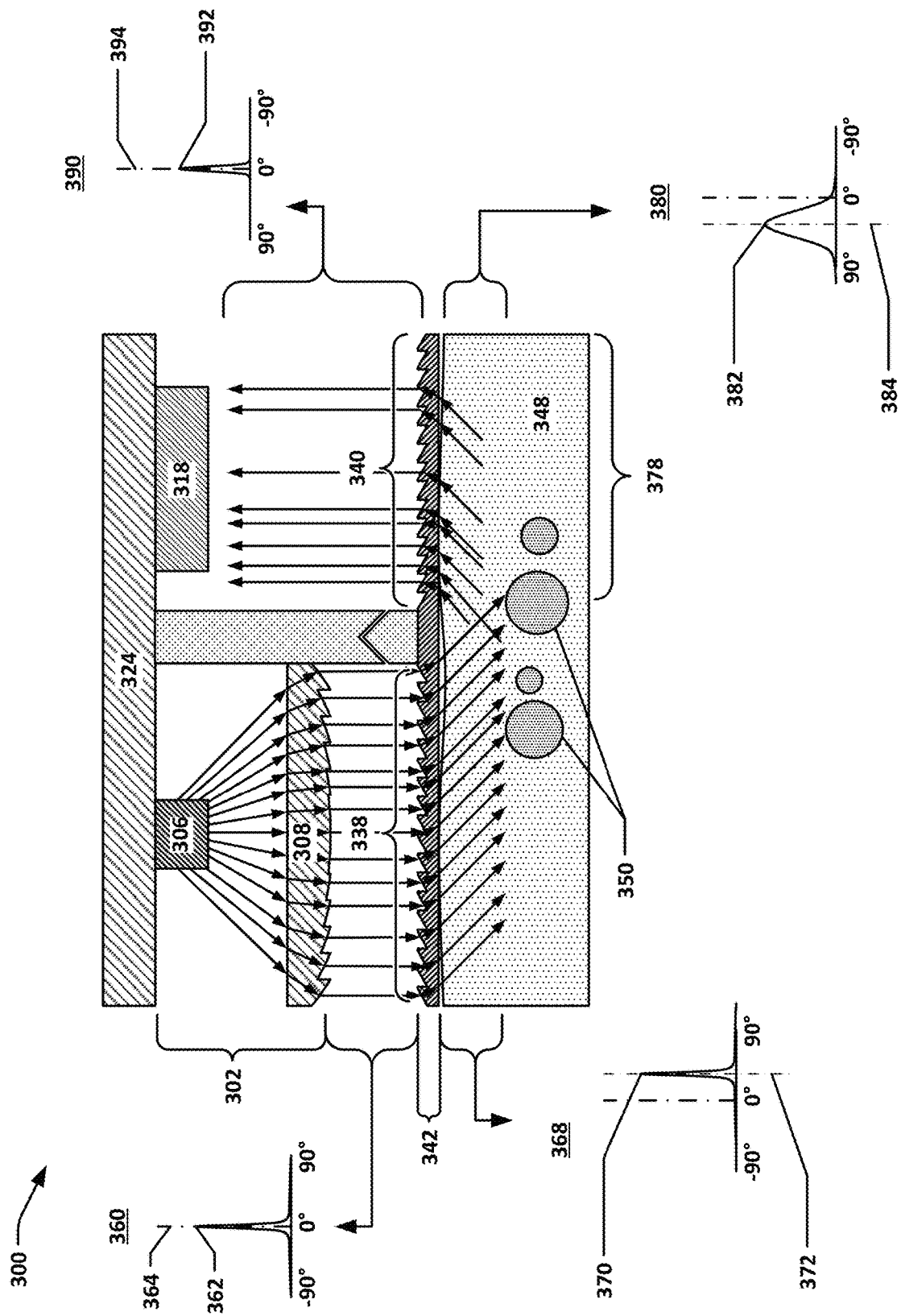
FIG. 3 depicts an example of an optical biological parameter sensor with a collimating light source assembly that includes a Fresnel lens.

FIG. 3 depicts an example of an optical biological parameter sensor with a collimating light source assembly that includes a Fresnel lens. In FIG. 3, an optical biological parameter sensor 300 is shown that includes a light source 306 and a Fresnel lens 308 that, in combination, act as a collimating light source assembly. Upon exiting the Fresnel lens 308, the partially or wholly collimated light may have a first angular distribution 360 having a first angular centroid 362 defining a first angular direction 364. The partially or wholly collimated light may then travel from the Fresnel lens 308 towards a first optical light field redirector 338 that, in this case, is provided by a number of prismatic reflecting/refracting elements arrayed across the first optical light field redirector 338. These prismatic reflecting/refracting elements, also referred to as light-turning features, may cause light that is received along directions generally parallel to the first angular direction 364 to be redirected such that the redirected light has a second angular distribution 368 with a second angular centroid 370 that defines a second angular direction 372. The angle between the second angular direction 372 and the first angular direction 364 may be an oblique angle, e.g., in the range of 5° to 50° or 10° to 50°.

Such angular ranges may also apply to other implementations discussed herein in which wholly or partially collimated light is redirected.

In this example implementation, the first optical light field redirector 338 is an integral part of a window 342, e.g., the window 342 may be formed with the light-turning features that redirect the light in one operation, e.g., through injection molding, or such features may be imparted to the window 342 through a separate process, e.g., by thermo-forming or stamping. Thus, for example, the window 342 may have a first transparent portion that overlays or extends over the collimating light source assembly 302 and that includes the first optical light field redirector 338 and a second transparent portion that overlays or extends over the first photodetector 318 and that includes one or more optical light field collection optics 340. In some implementations, the transparent portions may simply be subregions of a larger, contiguous transparent portion, whereas in some other implementations, the transparent portions may be discontiguous portions, e.g., separated by opaque portions of the window 342. The one or more optical light field collection optics 340 may be provided by one or more optical elements, e.g., lenses, diffractive optics, prismatic structures, etc., that may be configured to redirector and/or focus light diffusively reflected out of the person's skin onto the photosensitive area of the first photodetector.

When the optical biological parameter sensor 300 is placed against the skin of a person, the redirected received wholly or partially collimated light may be transmitted into the dermis 348 of the person after it exits the first optical light field redirector 338. Upon entering the dermis 348, the light may diffusively reflect off of the dermis 348 and, for example, blood vessels 350. The light that is then diffusively reflected back out of the dermis 348, i.e., sample-modulated light 378, and that passes through the window 342 may have a third angular distribution 380 with a third angular centroid 382 that defines a third angular direction 384. As can be seen, the third angular distribution 380 is much broader than the first angular distribution 360 or the second angular distribution 368; this is because the diffusive reflection of the sample-modulated light 378 has caused more of the light to travel along directions that are further from the third angular direction 384 as compared with the light of the first angular distribution 360 or the second angular distribution 368. The sample-modulated light may be thought of as traveling along a direction having a directional component opposite the first angular direction.

The sample-modulated light 378 may pass through the one or more optical light field collection optics 340, which may, as with the first optical light field redirector 338, be an integral part of the window 342 or be a separate component. The one or more optical light field collection optics 340 may collect and/or redirect the sample-modulated light 378 such that it has a fourth angular distribution 390 with a fourth angular centroid 392 defining a fourth angular direction 394. In this example, the optical light field collection optics 340 may be a series of prismatic light-turning structures that may act to redirect diffusively reflected light that may still have a strong directional component, e.g., as may be the case when the light enters and exits the skin at locations closely spaced together, thus resulting in a lower amount of diffusive reflection than may occur in situations where the light enters and exits the skin at locations spaced further apart. Thus, the optical light field collection optics 340 may primarily redirect such light without necessarily concentrating the light. The fourth angular direction 394 may be at an angle with respect to the third angular direction 384, such that the redirected sample-modulated light 378 is oriented more towards the first photodetector 318 than the non-redirected sample-modulated light 378. Such an arrangement may increase the amount of light from the light source 306 that is ultimately coupled into the dermis 348 while simultaneously also increasing the amount of diffusively reflected sample-modulated light 378 that reaches the first photodetector 318, thereby increasing the efficiency and performance of the optical biological parameter sensor 300.

The optical biological parameter sensor 300 also includes a feature on the first light barrier 328 that may mechanically interface with a complementary feature on the window 342, e.g., a complementary portion of the light barrier 328 that is bonded to or otherwise part of the window 342. Such features are more fully described in U.S. Provisional Patent Application No. 62/233,220, which is hereby incorporated herein by reference in its entirety; any of the interlocking or intermeshing features described in the 62/233,220 application may be used in place of the depicted features. In this example, the feature is a triangular groove in the first light barrier 328 that interfaces with a triangular ridge protruding out of the window 342. Such a feature may help prevent light leakage between the first light barrier 328 and the window 342 by removing any potential direct optical paths that may exist in a potential gap between the first light barrier 328 and the window 342. Thus, the light from the collimating light source assembly 302 may not have a direct optical path from the side of the first light barrier 328 facing the collimating light source assembly 302 to the side of the first light barrier 328 facing the first photodetector 318. Such complementary interface features may be implemented in a similar fashion in other implementations discussed herein, but are only illustrated in FIG. 3.

Figure 4:
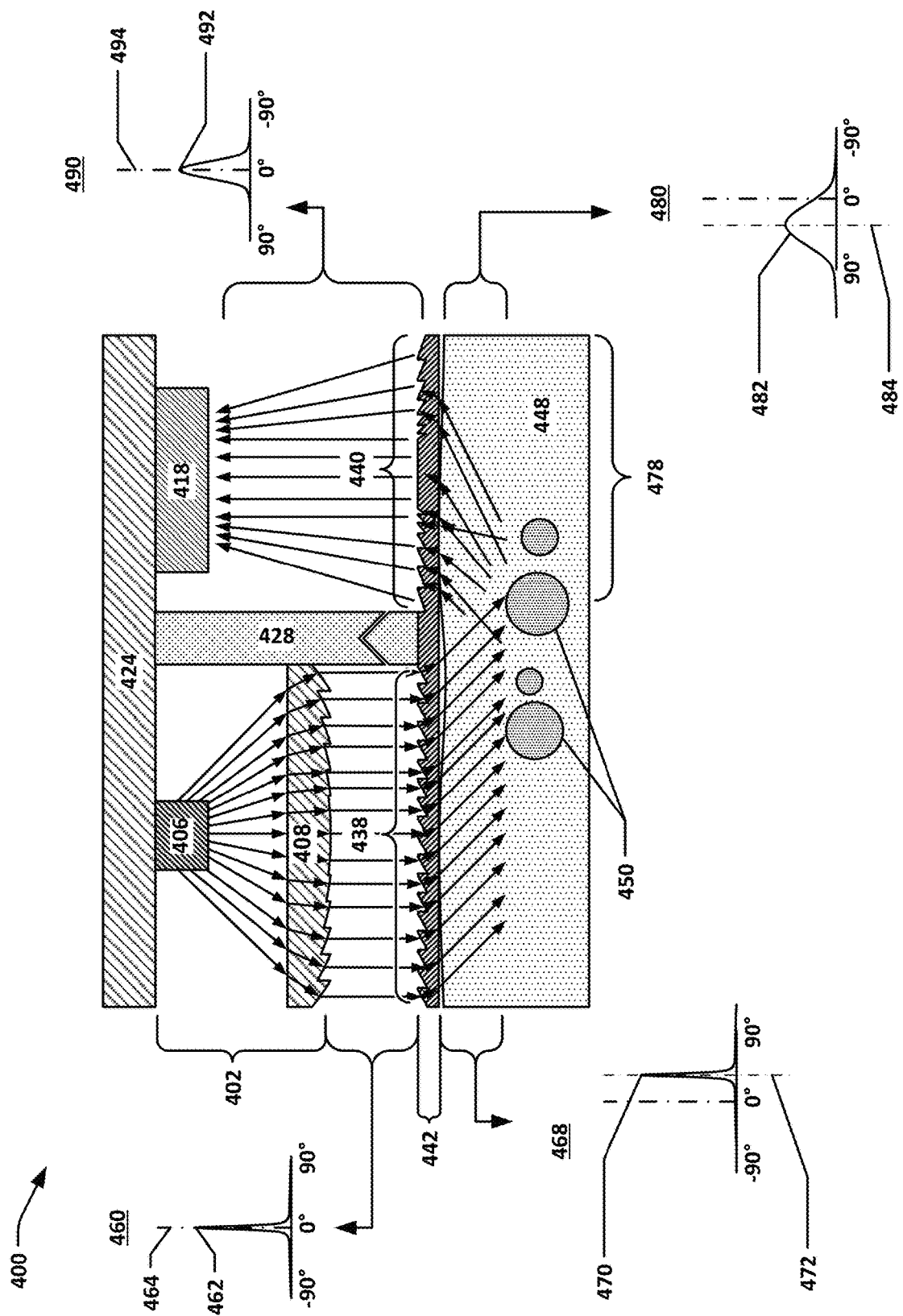
FIG. 4 depicts another example of an optical biological parameter sensor with a collimating light source assembly that includes a Fresnel lens.

FIG. 4 depicts another example of an optical biological parameter sensor with a collimating light source assembly that includes a Fresnel lens. FIG. 4 is, in many respects, similar to FIG. 3, and like components are indicated by callouts sharing the same last two digits. The above discussion of the components shown in FIG. 3 is applicable to the corresponding components of FIG. 4, with the exception of the optical light field collection optics 440, and is not reproduced here in the interest of conciseness.

The optical light field collection optics 440 in this example are arranged to provide a lensing effect and thus concentrate the diffusively reflected, sample-modulated light emanating from the dermis 448 on the first photodetector 418 in addition to potentially providing some light redirection functionality. This arrangement may be well-suited to optical biological parameter sensors in which the light enters and exits the skin at more widely-spaced locations, which may allow for increased diffusive reflection and a decrease in the directionality of the sample-modulated light that exits the dermis 448.

Figure 5:
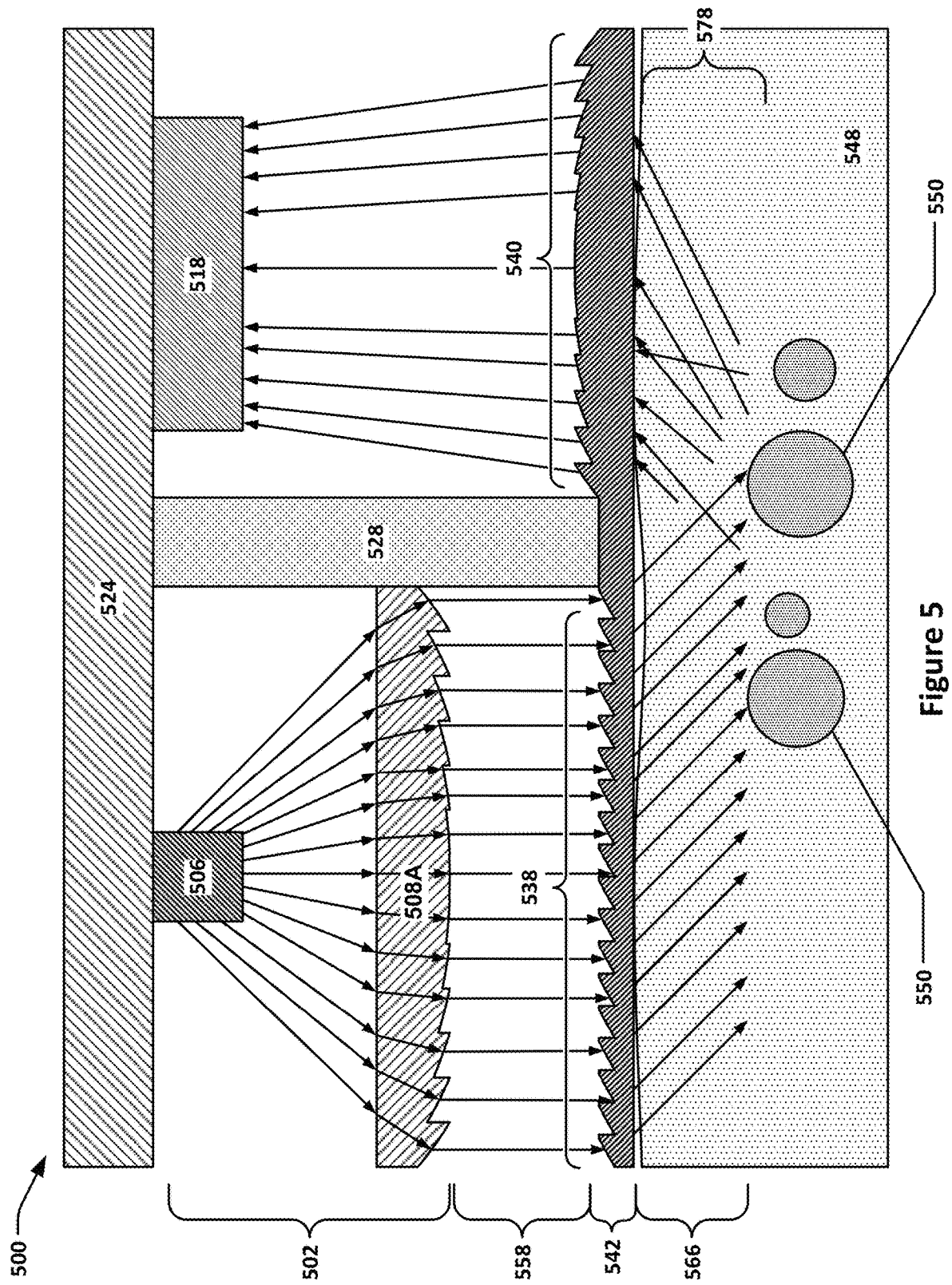
FIG. 5 depicts an example of an optical biological parameter sensor similar to the optical biological sensor of FIG. 3.

FIG. 5 depicts an example of an optical biological parameter sensor similar to the optical biological sensor of FIG. 3. In FIG. 5, an optical biological parameter sensor 500 is depicted. Many of the elements in the optical biological parameter sensor 500 are similar to the elements of the optical biological parameter sensor 300 of FIG. 3. In the interest of conciseness, such similar elements, which are indicated by callouts sharing the same last two digits, may not be described herein, except, for example, to note aspects in which such components differ. The discussion of the corresponding components with respect to FIG. 3 may be referred to for explanation of how such components may operate in the context of FIG. 5.

In FIG. 5, the one or more optical light field collection optics 540 are provided by way of a second Fresnel lens 508B (the first Fresnel lens, which is part of the collimating light source assembly, is denoted by callout 508A). The second Fresnel lens 508B may act to not only redirect the sample-modulated light 578, but to also focus it on a smaller area, e.g., to concentrate it on the first photodetector 518. This may further increase the efficiency of the first photodetector 518's ability to collect sample-modulated light 578.

A lens such as the second Fresnel lens 508B may differ from an optical light field redirector in that an optical light field redirector may typically redirect light without causing the divergence/convergence of the light to change appreciably, whereas a lens may redirect light in a manner that causes the convergence or divergence of the light to change. For example, a lens may allow light passing through the center of the lens to pass through the lens with little or no change in direction, but may cause light passing through the lens at other locations to change direction such that it converges on a focal point of the lens. Thus, for example, the half-height width of the angular distribution of light prior to passing through a lens is typically larger than the half-height width of the angular distribution of light after passing through a lens.

Figure 6:
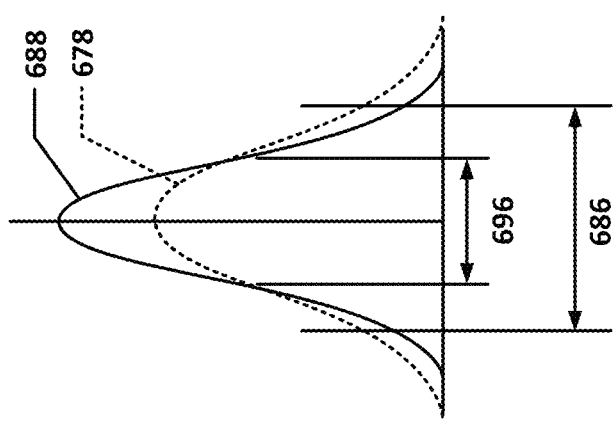
FIG. 6 depicts an example plot showing example angular distributions of light both before and after passing through a lens.

FIG. 6 depicts an example plot showing example angular distributions of light both before and after passing through a lens. An angular light distribution 678 is shown in a dotted line, and is representative of, for example, light prior to passing through a lens. The angular light distribution 678 may be described as having a bell-curve shaped distribution, and has a half-height width 686. An angular light distribution 688 is also shown using a solid line, and is representative of the same light after passing through the lens. As can be seen, the half-height width 696 of the angular light distribution 688 is smaller than the half-height width 686 of the angular light distribution 678. This is due to the focusing effect of the lens, which increases the intensity of the light along the focal axis of the lens (the center of the distributions, in this case), while reducing the intensity of light at the outer edges of the distributions.

Figure 7:
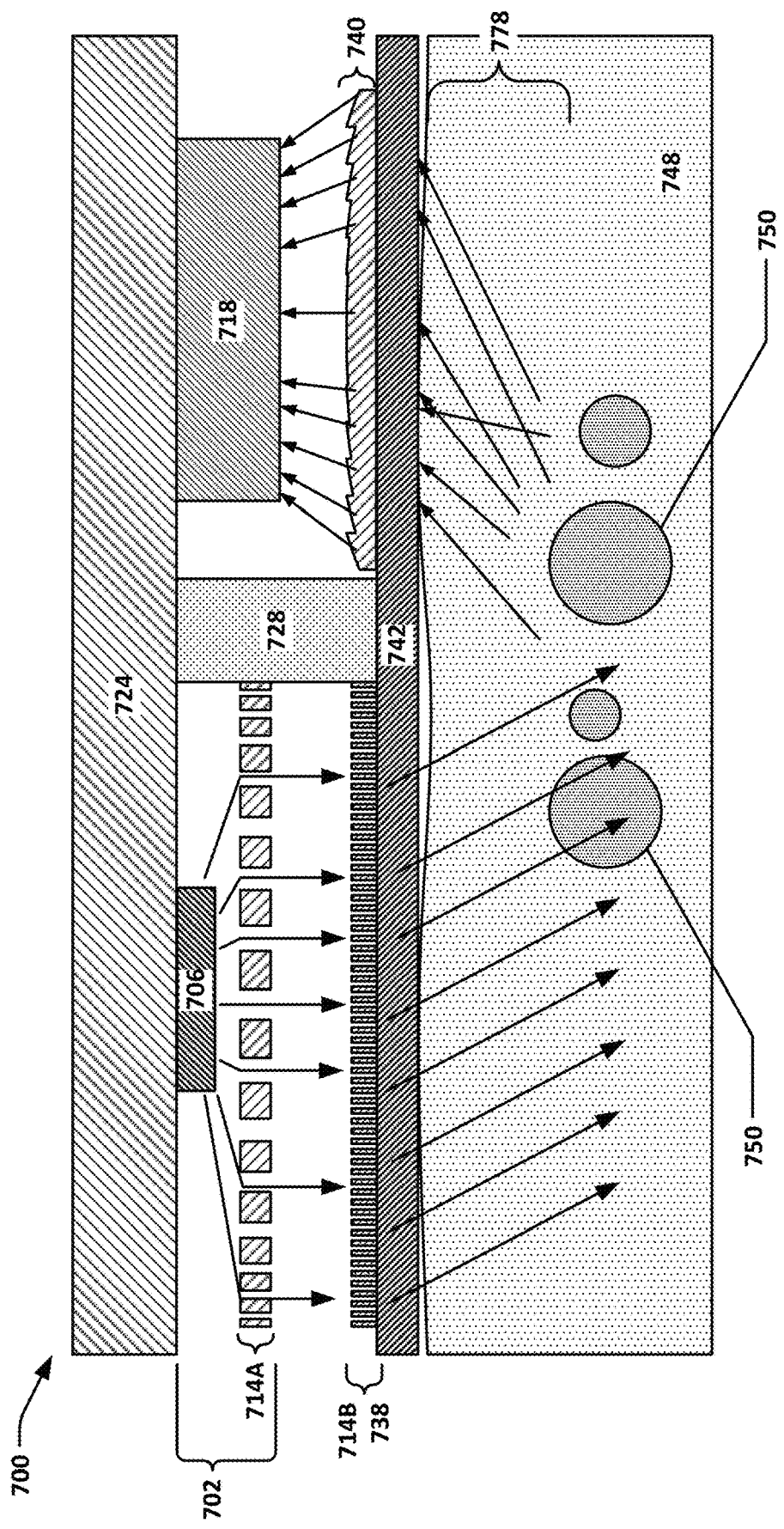
FIG. 7 depicts an example of an optical biological parameter sensor that uses diffractive gratings for some optical components.

FIG. 7 depicts an example of an optical biological parameter sensor that uses diffractive gratings for some optical components. In FIG. 7, an optical biological parameter sensor 700 is depicted that includes a collimating light source assembly 702 that is provided by a light source 706 and a first diffractive optic 714A. The first diffractive optic 714A may have a pattern of slits in it that are spaced apart from one another by a distance that decreases with increasing distance from the center of the light source 706; at the same time, the width of each slit may also decrease with increasing distance from the light source 706. Such a first diffractive optic 714A may have a collimating effect on the light that is emitted from the light source 706.

After exiting the first diffractive optic 714A, the partially or wholly collimated light may enter a second diffractive optic 714B, which may feature a pattern of slits with constant spacing and constant widths; the second diffractive optic 714B may serve as the first optical light field redirector 738 and shift the average direction of the partially or wholly collimated light so as to have a larger directional component directed towards the first photodetector 718. Such redirected wholly or partially collimated light may pass through a window 742 then enter a person's skin and dermis 748, where it may diffusively reflect from the dermis 748 and from, for example, blood vessels 750 and emanate out of the person's skin as sample-modulated light 778. The sample-modulated light 778 may then pass back through the window 742 and a Fresnel lens 708, which may concentrate the sample-modulated light 778 on the first photodetector 718.

Figure 8:
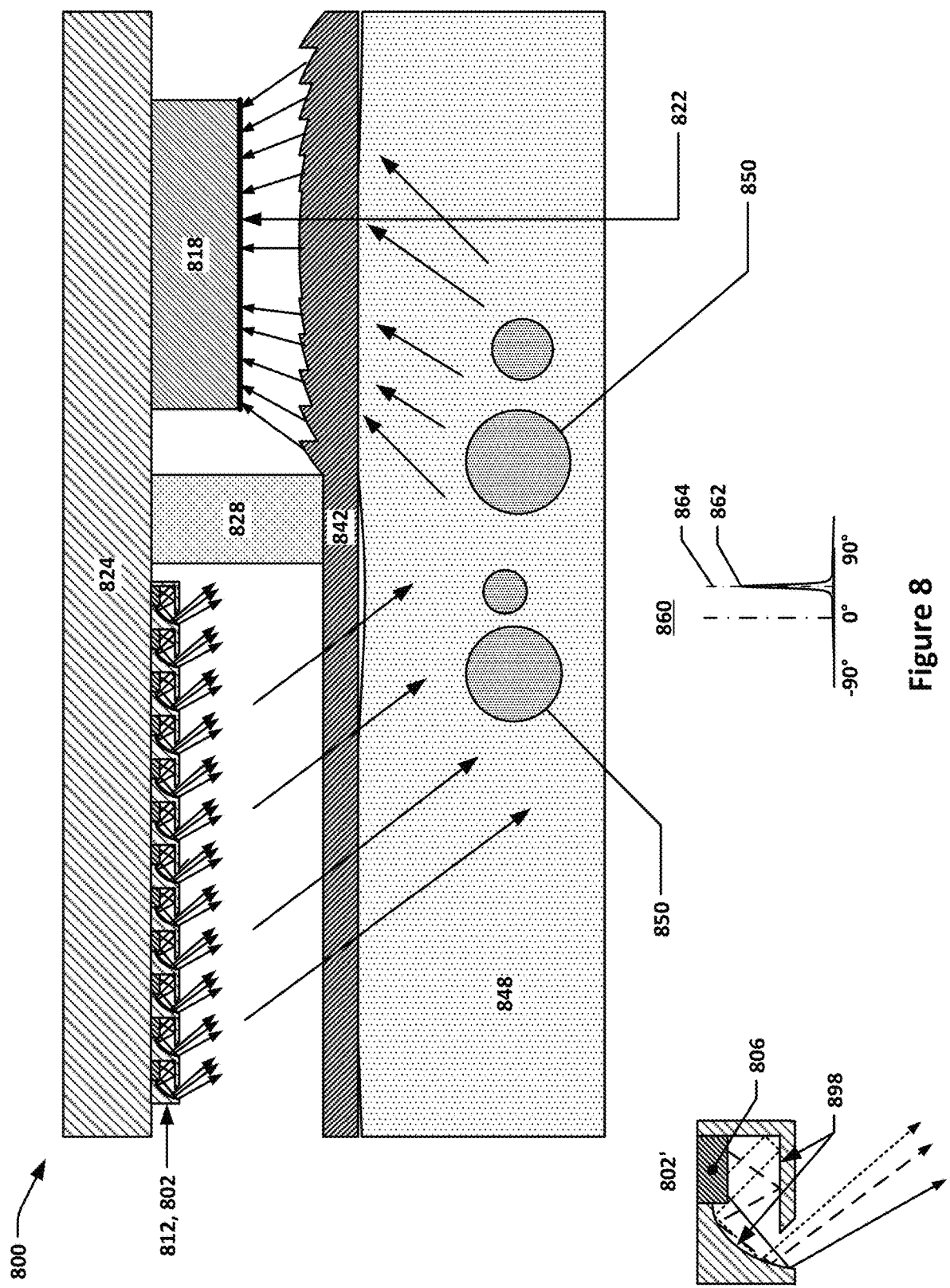
FIG. 8 depicts an optical biological parameter sensor that utilizes an array of light sources coupled with light-steering collimator features.

FIG. 8 depicts an optical biological parameter sensor that utilizes an array of light sources coupled with light-steering collimator features. FIG. 8 depicts an optical biological parameter sensor 800 that includes a collimating light source assembly 802. The collimating light source assembly 802, in this implementation, is provided by an array 812 of collimating light source pixels 802'. Each collimating light source pixel 802' may include a light source 806, e.g., an LED, and a reflective surface 898 that may be configured to reflect light rays emitted from the light source 806 such that the light exits the light source pixel 802 as partially or wholly collimated light and along an average direction that has a directional component oriented towards a first photodetector 818. For example, the array 812 may emit partially or wholly collimated light that has a first angular distribution 860 with a first angular centroid 862 that defines a first angular direction 864 (with respect to an axis that is normal to a substantially planar surface 822 of the first photodetector 818); the first angular direction 864 may define the average direction discussed above. In this implementation, the collimation and light-steering functionality provided by separate optical systems in the previously discussed implementations are provided by a single optical system.

The collimated and steered light emitted by the collimating light source assembly 802 may pass through a window 842 and be directed into a person's dermis 848, where it may diffusively reflect off the dermis 848 and blood vessels 850 in the dermis 848. The diffusively reflected light may re-enter the window 842 and, for example, be concentrated on the first photodetector 818 by a Fresnel lens (pictured) or other optical feature.

In the previous examples of optical biological parameter sensors, the photodetector(s) and light sources have general been mounted to the same substrate and have thus generally had active surfaces that are parallel to one another. As many collimating light source assemblies may emit light primarily along a direction normal to the substrate on which the light source is mounted, the optical light field redirectors discussed earlier herein may be needed to tilt the wholly or partially collimated light towards the first photodetector. However, tilting of the wholly or partially collimated light may also be accomplished by tilting the collimating light source assembly itself instead of redirecting the partially or wholly collimated light after it is emitted by the collimating light source assembly.

Figure 9:
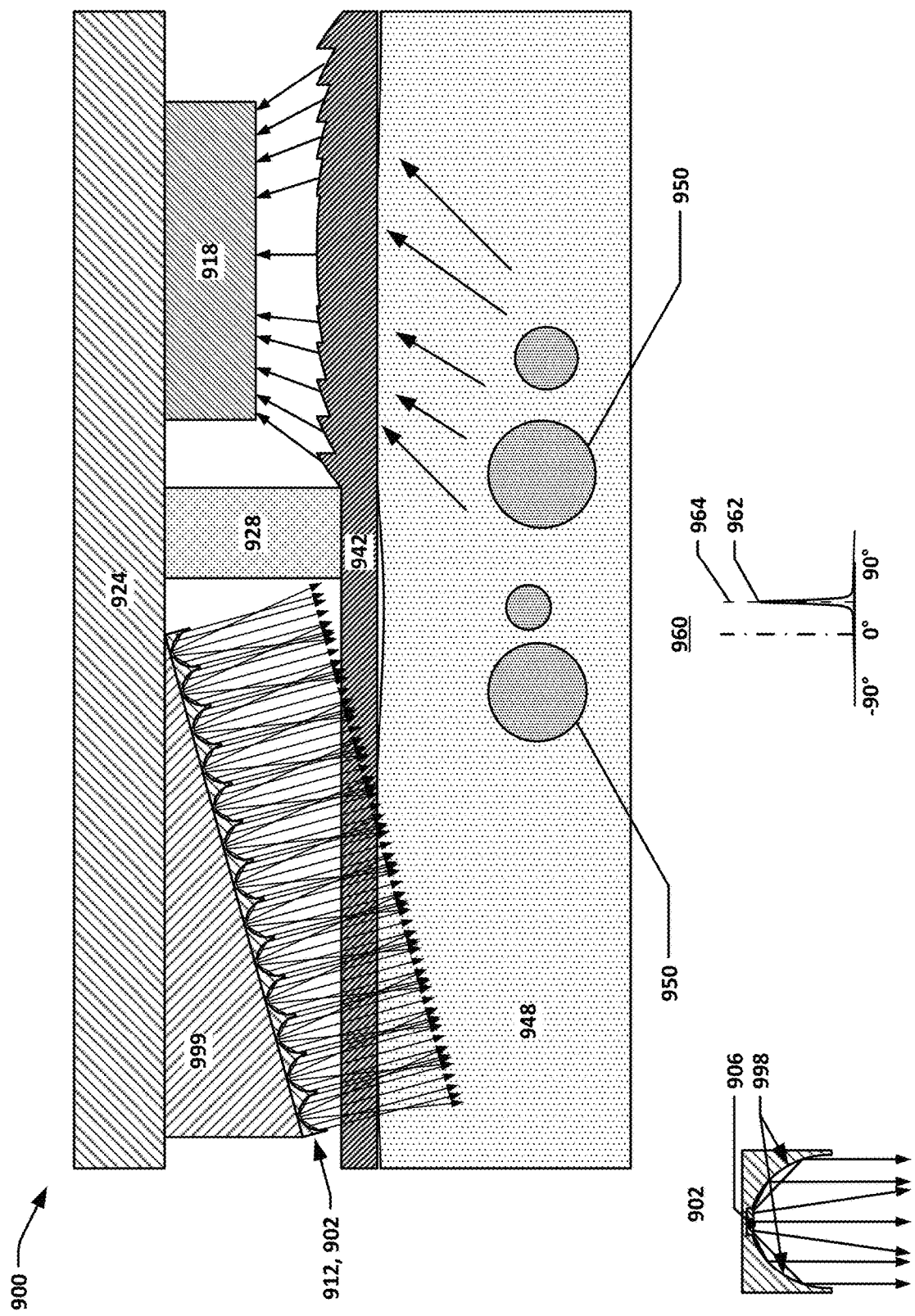
FIG. 9 depicts an example of an optical biological parameter sensor that has a tilted collimating light source assembly.

FIG. 9 depicts an example of an optical biological parameter sensor that has a tilted collimating light source assembly. An optical biological parameter sensor 900 is shown in FIG. 9; the optical biological parameter sensor 900 may include a substrate 924 with a first photodetector 918 and a collimating light source assembly 902, which, in this example, is provided by an array 912 of collimating light source pixels 902' that is positioned so as to be at an oblique angle with respect to the substrate 924, e.g., by a wedge 999 or other structure. The first photodetector 918 The wedge 999 may include circuitry (not shown) to electrically connect the collimating light source pixels 902' in the array 912 with circuitry in the substrate 924. Alternatively, the array 912 of collimating light source pixels 902' may be mounted to a flexible substrate, e.g., a flexible printed circuit, that is supported by the wedge 999 and that is electrically connected with circuit traces in the substrate 924 or with other mechanisms allowing for power and control signals to be sent to the collimating light source pixels. Alternatively, the collimating light source pixels 902' may be mounted to a small, rigid substrate, e.g., a printed circuit board, that is supported by the wedge 999 and that is electrically connected with the substrate or other mechanism for providing data and/or power signals by a cable or flexible printed circuit.

As can be seen in the detail view (lower left corner of Figure) of one of the collimating light source pixels 902', each collimating light source pixel 902' may include a light source 906 that is positioned within a parabolic or otherwise curved reflector having a reflective surface 998. Divergent light that is emitted by the light source 906 may reflect off of the reflective surface 998 such that the divergent light that is emitted by the collimating light source assembly pixel 902 is partially or wholly collimated (in this example, the light will only be partially collimated since some of the divergent light may exit the collimating light source pixel 902' without reflecting off of the reflective surface 998; other types of reflectors may provide more collimation). Thus, the light that is emitted by the array 912 may be partially or wholly collimated and, by virtue of the angled positioning of the array 912, the angular direction associated with the angular centroid of the angular distribution of the partially or wholly collimated light may have a directional component that is directed towards the first photodetector 918 without using a separate optical light field redirector. For example, the partially or wholly collimated light may have a first angular distribution 960, with respect to a normal vector of the substrate 924 or the substantially planar photosensitive surface of the first photodetector 918, with a first angular centroid 962 that defines a first angular direction 964. The first angular direction 964 may, for example, be within 5° and 50° of such a normal vector.

Figure 10:
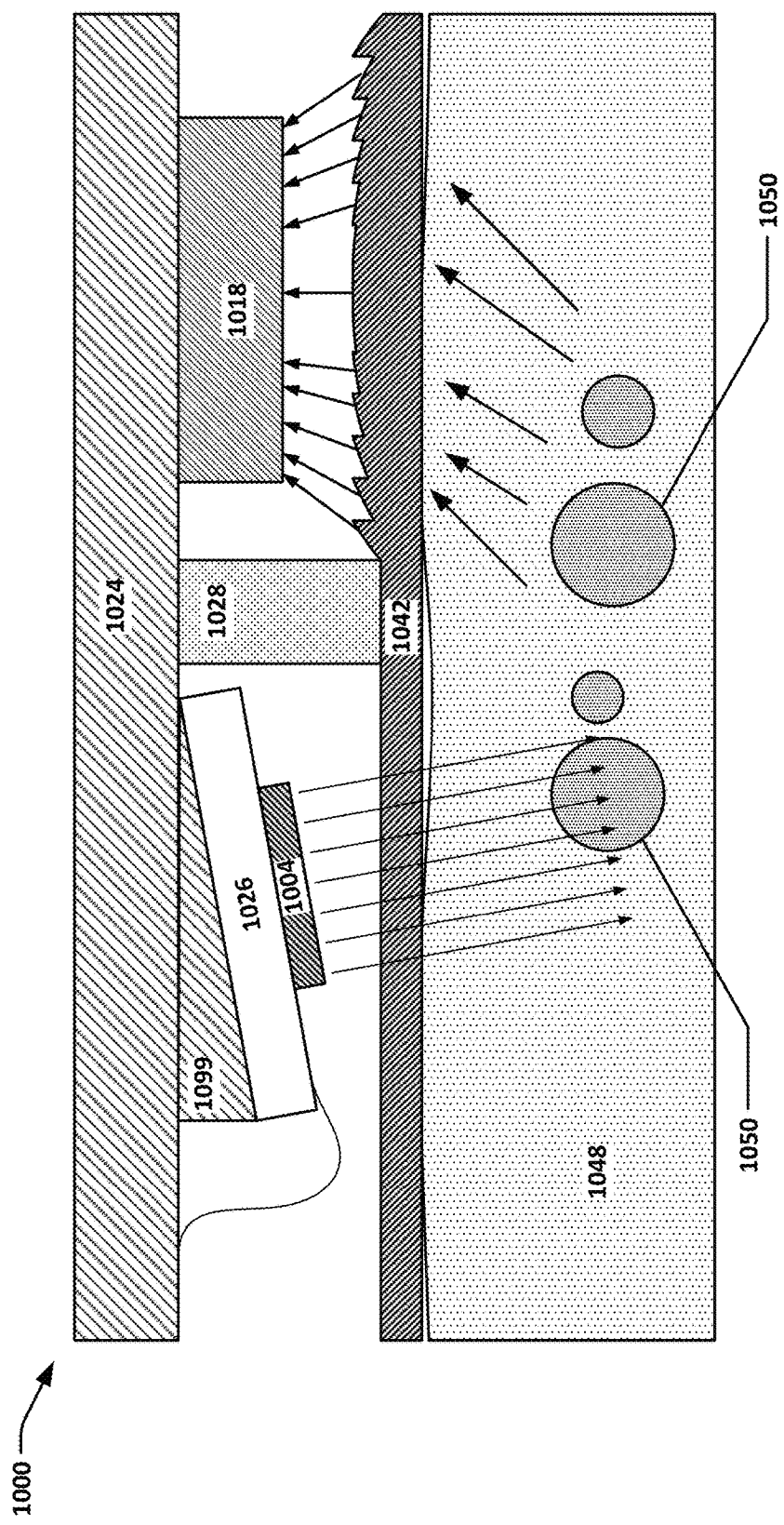
FIG. 10 depicts an example of an optical biological parameter sensor in which a coherent light source is used as a collimating light source assembly.

FIG. 10 depicts an example of an optical biological parameter sensor in which a coherent light source is used as a collimating light source assembly. FIG. 10 depicts a substrate 1024 that supports a first photodetector 1018 and a wedge 1099 or other structure that may be used to support a printed circuit 1026 (rigid or flexible) that interfaces with, for example, a surface-emitting laser diode 1004. The wedge 1099 or other structure may tilt the light beam emitted by the surface-emitting laser diode 1004 such that the light beam follows a direction that forms an angle of approximately 5° to 50° with respect to a normal vector of the substrate 1024 or the photosensitive area of the first photodetector 1018. This is similar to the approach taken in the implementation of FIG. 9, and has similar effects. In some implementations, the wedge 1099 or other structure that supports the surface-emitting laser diode 1004 may be provided by, for example, a flexible printed circuit or other electrical routing component that has been folded into so as to position the surface-mount laser diode 1004 at the desired angle. A surface-emitting laser is a laser component that emits light in a direction that is generally normal to the substrate to which the surface-emitting laser is mounted. The surface-mount laser diode may provide partially or wholly collimated light, e.g., coherent light, when powered. The partially or wholly collimated light may pass through a window 1042 before entering a person's dermis 1048, where it may be diffusively reflected by the dermis 1048 and/or blood vessels 1050 before passing back through the window 1042 and reaching the first photodetector 1018. The window 1042 may optionally include an optical element, such as the depicted Fresnel lens, that may serve to focus or redirect such diffusely reflected light onto the first photodetector 1018. In this example, a first light barrier 1028 is shown that may be interposed between the surface-mount laser diode 1004 and the first photodetector 1018, although, as discussed further below, such a barrier may be unnecessary in some implementations.

It is to be understood that while many of the examples discussed herein have involved single light sources and single photodetectors, such features also may be provided by clusters, arrays, or other examples of multiple such features. For example, instead of a single photodetector element, a pixelated array of photodetector elements may be used. Such an array may be rectangular, or may, for example, be circular, e.g., a circular array of photodetector elements arranged around the light source. Similarly, the light source may, as with some of the example implementations provided herein, be provided by an array of multiple light sources, e.g., an array of LEDs.

It is also to be understood that the light barriers depicted in the examples herein may be omitted in some implementations. For example, if the collimating light source assembly and the optical light field redirector are configured such that there is little or no risk of light from the collimating light source assembly reaching the photodetector(s) before passing into a person's skin and thereby being turned into sample-modulated light, then the use of a light barrier may be redundant. In such cases, the light barriers may simply be omitted, if desired.

It is to be further understood that the light-transmission structures, i.e., the structures that are "upstream" of the dermis/epidermis, and the light-reception structures, i.e., the structures that are "downstream" of the dermis/epidermis, shown in the various implementations discussed herein may be used in other combinations than the specific combinations shown. For example, any of the collimating light source assemblies discussed herein, as well as other collimating light source assemblies, may be used in the place of any specific example collimating light source assembly of any of the implementations depicted herein. By way of further example, a surface-mount laser light source may be used in place of an LED light source and diffractive optic to provide a collimating light source assembly, and the light therefrom may then be redirected using an optical light field redirector.

The light sources discussed herein may be broad-spectrum, e.g., white light, or may be designed to provide light concentrated within certain spectral bands, e.g., red light, infrared light, yellow light, and/or green light. The particular wavelengths used may be selected based on the optical biological parameter to be determined. For example, light sources emitting primarily green wavelength light may be well-suited to measuring heart rate, but red light and infrared light sources may be more well-suited to measuring blood oxygenation level.

The effects of using light-steering features can have dramatic impact on the strength of a PPG signal. This is illustrated in the following Figures and discussion.

Figure 11:
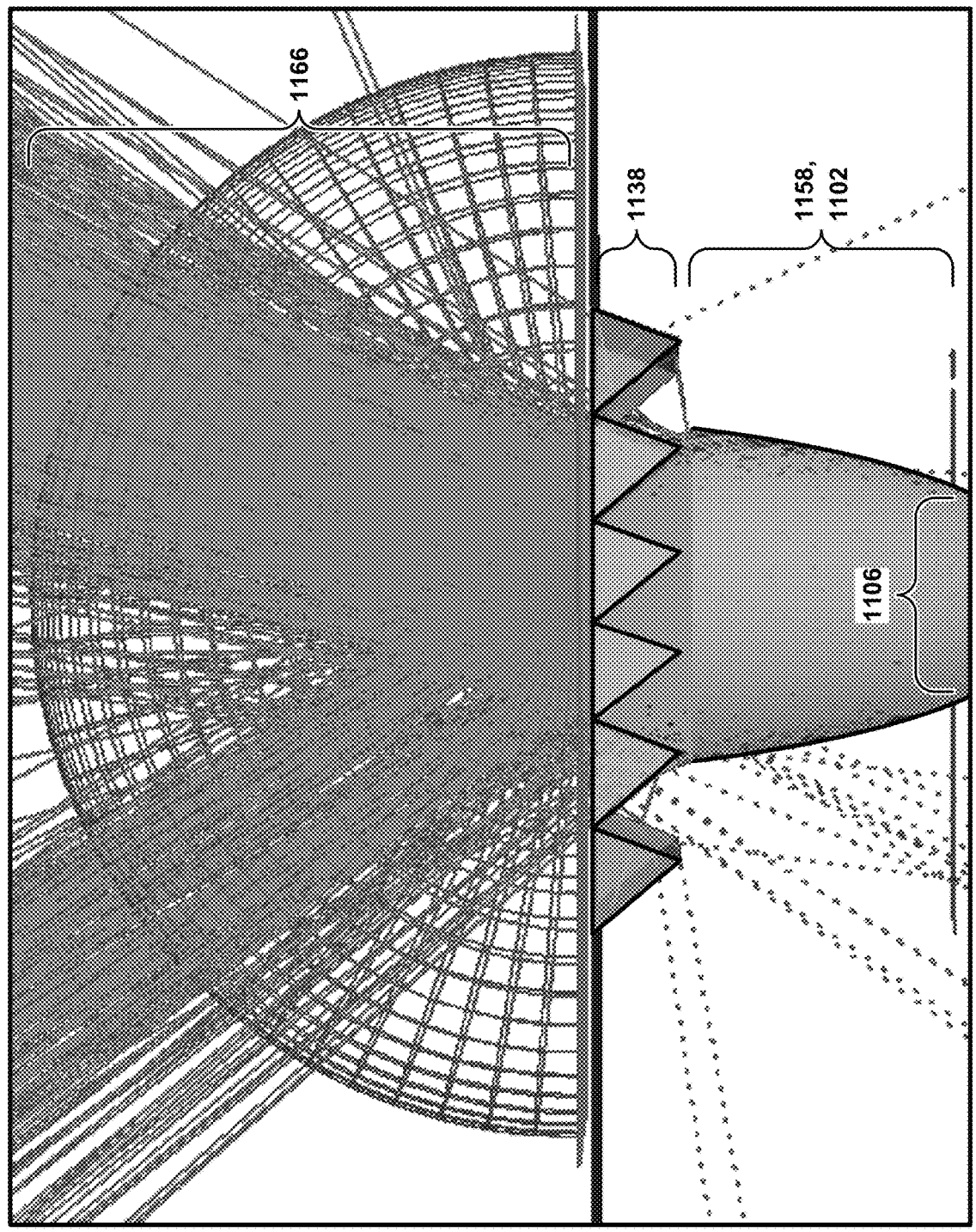
FIG. 11 depicts a simulation result showing ray tracings for a light source with a collimating light source having a parabolic reflector and an optical light field redirector having a Fresnel lens.

FIG. 11 depicts a simulation result showing ray tracings for a light source with a collimating light source having a parabolic reflector and an optical light field redirector having a Fresnel lens. In FIG. 11, a collimating light source 1102 is shown; the collimating light source may include a parabolic reflector (the side walls of which are depicted) that may emit partially or wholly collimated light 1158 that is introduced by a light source 1106 located at the bottom of the parabolic reflector. The partially or wholly collimated light 1158 may then pass through a first optical wavefront redirector 1138, which is, in this case, a Fresnel lens/prism. As can be seen, while some of the partially or wholly collimated light 1158 received by the first optical wavefront redirector 1138 is directed to the left as redirected received partially or wholly collimated light 1166, most of the partially or wholly collimated light 1158 received by the first optical wavefront redirector 1138 is directed to the right as redirected received partially or wholly collimated light 1166 (as evidenced by the increased density of rays on the right side of FIG. 11 as compared with the left side).

FIG. 12 is a picture of an example biometric monitoring device with a PPG sensor having a square photodetector interposed between a left light source equipped with a parabolic reflector and Fresnel lens arrangement as simulated in FIG. 11 and a right light source that does not include the Fresnel lens arrangement (although it does include the same parabolic reflector). The four circles along the bottom edge are electrical contacts for charging purposes and are not optical features. FIG. 12' is a photograph taken of the example biometric monitoring device of FIG. 12 with the light sources activated while a white projection surface is held perpendicular to the photodetector and generally in-line with the light sources so as to show the beam dispersion patterns produced by each light source. The photograph of FIG. 12' has been post-processed (the negative image of the original is shown in the upper left corner in greyscale—the light sources used were green light-emitting diodes) to more clearly show contours of different light intensity bands (the darker the band, the greater the light intensity), and has been augmented with annotations showing the two photoemitters (PE), the photodetector (PD), and the edge (the dash-dot-dash line) of the projection surface resting on the biometric monitoring device. FIG. 12' also includes three white arrows, the middle one of which indicates the normal to the photodetector active area, the left of which highlights the direction of maximum intensity of the light emitted from the left light source, and the right of which highlights the direction of maximum intensity of the light emitted from the right light source. As is clearly evident, the use of light-steering features as discussed herein in the left light source results in a clear biasing of the emitted light towards the photodetector, which will result in a stronger PPG signal at the photodetector. In contrast, the right light source has a lower intensity and is not biased towards the photodetector.

Figure 13:
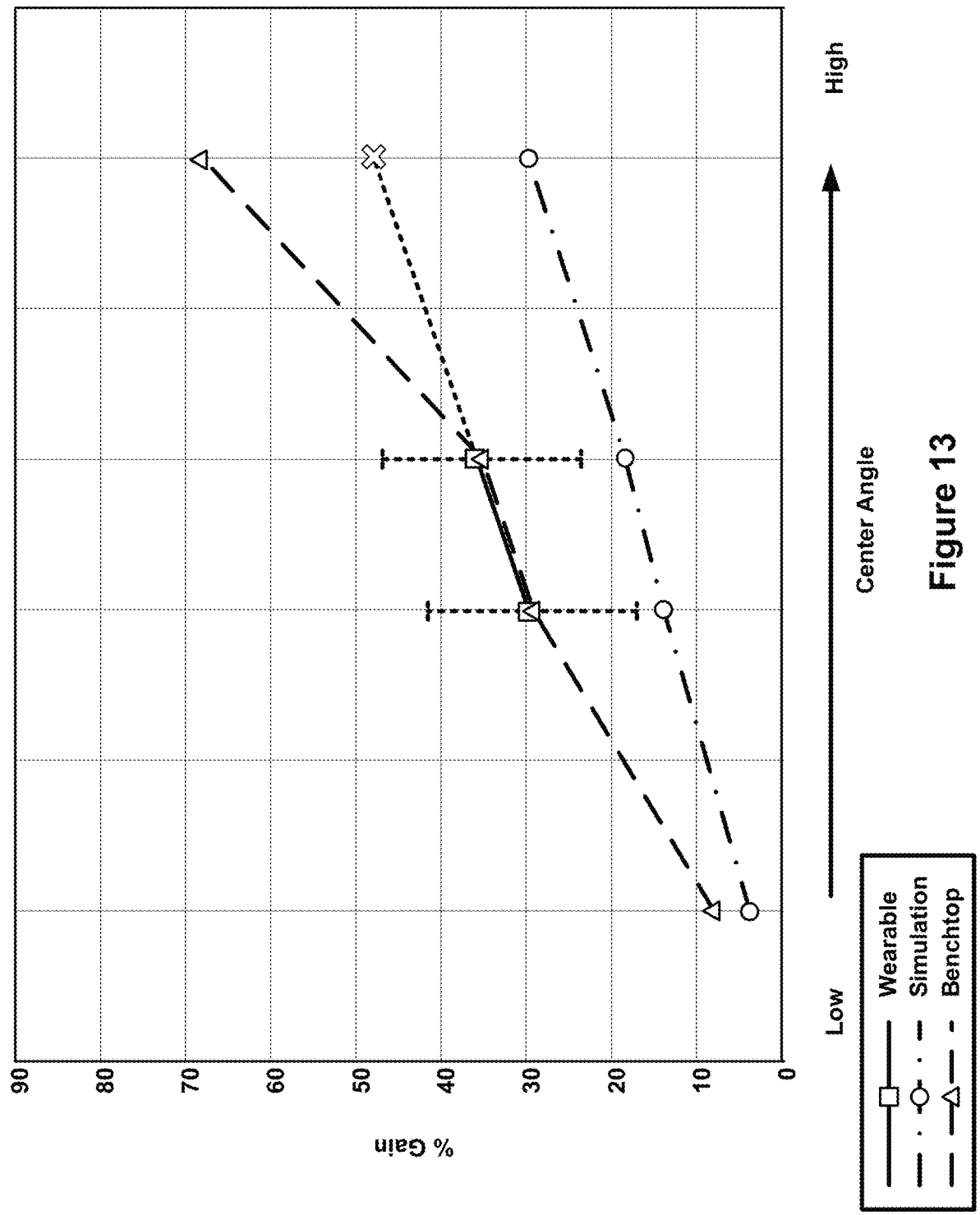
FIG. 13 depicts data from simulations and test measurements that shows AC signal intensity as a function of light incidence angle.
Figure 14:
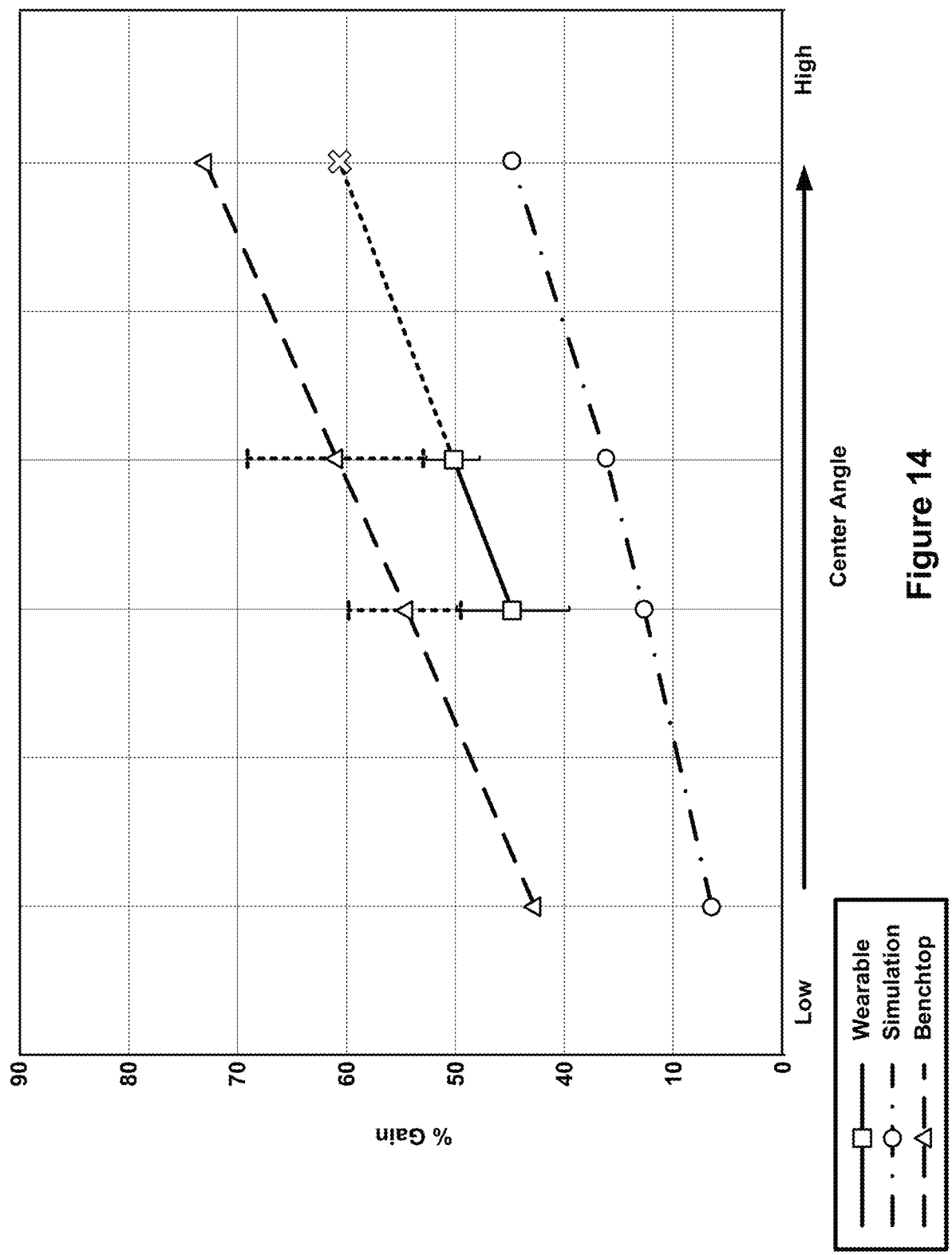
FIG. 14 depicts data from simulations and test measurements that shows DC signal intensity as a function of light incidence angle.

FIG. 13 depicts data from simulations and test measurements that shows AC signal intensity as a function of light incidence angle. FIG. 14 depicts data from simulations and test measurements that shows DC signal intensity as a function of light incidence angle. In both FIGS. 13 and 14, the percentage gain of signal intensity at the photodetector of a PPG sensor similar to that shown in FIGS. 11 and 12 is shown as a function of increasing angle from a vector that is normal to the photodetector active surface area, e.g., the angle between the angle of maximum light intensity and, for example, the vector indicated by the middle white arrow in FIG. 12'. This angle is referred to as the "center angle" in these Figures. The percentage gain is determined by comparing the signal intensity within a predefined cone angle with a center axis at the center angle against the signal intensity within that same predefined cone angle with a center axis that is, in effect, perpendicular to the substrate/light source emission plane (unsteered—similar to the right light source in FIG. 12'). The percentage gain is shown relative to the signal for a non-light-steered implementation, e.g., a center angle of 0°. Three data sets are shown in each Figure—one data set (circles) showing the results of a Monte Carlo light transport simulation, another data set (triangles) showing measurements averaged across 5 users using a benchtop test setup that allowed the light to be directed along four different angles (the error bars show the standard error for these measurements), and a third data set (squares) showing measurements taken with the light sources in the test device shown in FIG. 12 (each light source was activated individually). The "X" markers show the predicted gain for a wearable device having light-steering features that cause the light to have a center angle as high as 50° off center. As can be seen, the use of light-steering features as discussed herein may result in a signal strength that is in the neighborhood of 30-50% higher than for non-light-steered implementations, which is a significant performance gain.

It is to be understood that the above concepts have focused on redirecting partially or wholly collimated light for an optical biological parameter sensor such that it is somewhat "tilted" towards the photodetector of the optical biological parameter sensor in order to increase the amount of light that is then diffusively reflected out of a person's skin and detectable by the photodetector. This may act to increase the signal strength.

However, it is to be understood that, in some scenarios, the opposite approach may be desirable. For example, in current optical biological parameter sensors, packaging and assembly considerations may practically limit the spacing between a light source and a photodetector such that a gap of at least 1 mm or more may exist between such components. However, continuing miniaturization of such components, as well as new packaging arrangements of such components, may lead to such a gap distance decreasing further. If this gap decreases too much, i.e., the photodetector and the light source are positioned too close together, the DC component of the diffusively reflected light may be sufficiently high that the photodetector may not be able to reliably detect the AC component of the diffusively reflected light due to saturation from the DC component. In such cases, it may be desirable to actually tilt the partially or wholly collimated light in the opposite direction, i.e., away from the photodetector, in order to increase the optical path length through the pulsating tissue in the sample, thus increasing the amount of AC modulation in the signal and increasing the AC/DC ratio of the sample-modulated light to allow the photodetector to more reliably detect the AC component of the sample-modulated light. Thus, it is to be understood that all of the concepts discussed above with respect to the depicted implementations may also be practiced so as to, in effect, reverse the tilt angle of the redirected light when evaluated with respect to either the first angular direction or with respect to a vector normal to the photodetector active area. Such further implementations may, as stated above, be beneficial in scenarios where the photodetector and light source are very closely spaced together, e.g., less than 1 mm apart.

Importantly, the concepts discussed herein are not limited to any single aspect or implementation discussed herein, nor to any combinations and/or permutations of such aspects and/or implementations. Moreover, each of the aspects of the present invention, and/or implementations thereof, may be employed alone or in combination with one or more of the other aspects and/or implementations thereof. For the sake of brevity, many of those permutations and combinations will not be discussed and/or illustrated separately herein.

What is claimed is:

1. An apparatus comprising:
   a wearable biological parameter sensor including:
   a substrate;
   a collimating light source assembly mounted to the substrate, the collimating light source assembly configured to emit light, wherein the light that is emitted by the collimating light source assembly when the collimating light source assembly is on is partially or wholly collimated light having a first angular distribution with a first angular centroid defining a first angular direction and wherein the first angular direction points away from the substrate;

one or more first photodetectors; and a first optical light field redirector positioned so as to receive, via one or more surfaces facing towards the collimating light source assembly, at least some of the partially or wholly collimated light emitted by the collimating light source assembly and configured to redirect the received partially or wholly collimated light such that the redirected received partially or wholly collimated light has, after exiting the first optical light field redirector via one or more surfaces facing away from the collimating light source assembly, a second angular distribution with a second angular centroid defining a second angular direction having a directional component extending towards the one or more first photodetectors to a greater extent than a corresponding directional component of the first angular direction, wherein the first optical light field redirector is optically transmissive and separate from the collimating light source assembly.

2. The apparatus of claim 1, further comprising a first light barrier interposed between the collimating light source assembly and the one or more first photodetectors.

3. The apparatus of claim 2, wherein the first light barrier has a first surface facing towards the collimating light source assembly and a second surface facing towards the one or more first photodetectors, wherein the first surface and the second surface define a mid-plane between them that is within ±10° of parallel with the first angular direction.

4. The apparatus of claim 2, wherein the first light barrier has a first surface facing towards the collimating light source assembly and a second surface facing towards the one or more first photodetectors, wherein the first angular direction is within ±10° of parallel with the average normal vector defined by the first surface and the second surface.

5. The apparatus of claim 2, further comprising a window with one or more transparent portions, wherein:

the first light barrier interfaces with the window such that light from the collimating light source assembly does not have a direct optical path from the side of the first light barrier facing towards the collimating light source assembly to the side of the first light barrier facing towards the one or more first photodetectors, one of the one or more transparent portions extends over the collimating light source assembly, one of the one or more transparent portions extends over the one or more first photodetectors, and the first optical light field redirector is provided by optical light-turning features molded into the window in the transparent portion extending over the collimating light source assembly.

6. The apparatus of claim 1, wherein the intensity of light in the second angular distribution associated with the first angular direction is less than the intensity of light in the first angular distribution associated with the first angular direction.

7. The apparatus of claim 1, further comprising control logic including a memory and one or more processors, wherein:

the memory, the one or more processors, the collimating light source assembly, and the one or more first photodetectors are operably connected, and the memory stores computer-executable instructions for controlling the one or more processors to:

cause the collimating light source assembly to emit light, obtain detected light measurements from the one or more first photodetectors in association with the emission of light from the collimating light source assembly, and determine a biological parameter based at least in part on the detected light measurements.

8. The apparatus of claim 7, wherein the memory stores computer-executable instructions for controlling the one or more processors to:

obtain a photoplethysmogram from the detected light measurements, and determine the biological parameter from the photoplethysmogram.

9. The apparatus of claim 7, wherein the biological parameter is selected from the group consisting of: heart rate, blood oxygen saturation ($SpO_2$), respiration rate, blood perfusion, hydration level, tissue oxygen saturation ($StO_2$), tissue metabolic rate, melanin composition, structural orientation of collagen tissue fibers, structural orientation of muscle fibers, bulk cell size, bulk cell density, extracellular matrix size, and extracellular matrix density.

10. The apparatus of claim 1, wherein the first angular direction and the second angular direction form an included angle between them of between 5° and 50°.

11. The apparatus of claim 1, wherein the collimating light source assembly includes:

a light source; and a Fresnel lens interposed between the light source and the first optical light field redirector, wherein the Fresnel lens is configured to partially or wholly collimate light from the light source and direct the partially or wholly collimated light towards the first optical light field redirector.

12. The apparatus of claim 1, wherein the collimating light source assembly includes:

one or more light sources; and one or more optical reflectors, wherein:

each optical reflector has a corresponding light source, and the one or more optical reflectors are configured to reflect light from the corresponding light sources to generate the partially or wholly collimated light having the first angular distribution.

13. The apparatus of claim 1, wherein the collimating light source assembly includes:

a light source; and a diffractive grating optic interposed between the light source and the first optical light field redirector, wherein the diffractive grating optic is configured to partially or wholly collimate light from the light source and direct the collimated light towards the first optical light field redirector.

14. The apparatus of claim 1, further comprising a window with one or more transparent portions, wherein:

one of the one or more transparent portions extends over the collimating light source assembly, one of the one or more transparent portions extends over the one or more first photodetectors, and the first optical light field redirector is provided by optical light-turning features molded into the window in the transparent portion extending over the collimating light source assembly.

15. The apparatus of claim 1, further comprising one or more optical light field collection optics positioned so as to receive sample-modulated light traveling along a first direction having a component opposite the first angular direction and to then direct the received sample-modulated light towards the one or more first photodetectors, wherein:
the received sample-modulated light has a third angular distribution with a third angular centroid defining a third angular direction, and
the one or more optical light field collection optics are configured to redirect the received sample-modulated light such that the redirected received sample-modulated light has a fourth angular distribution with a fourth angular centroid defining a fourth angular direction that is tilted away from the one or more first photodetectors to a lesser extent than the third angular direction.

16. The apparatus of claim 1, further comprising an optical lens positioned so as to receive sample-modulated light traveling along a first direction having a directional component opposite the first angular direction and having a third angular distribution with a first half-height width, wherein:
the optical lens is configured such that the sample-modulated light, after passing through the optical lens, has a fourth angular distribution with a second half-height width that is less than the first half-height width.

17. The apparatus of claim 1, further comprising:
one or more second photodetectors; and
a second optical light field redirector positioned so as to receive at least some of the partially or wholly collimated light emitted by the collimating light source assembly and configured to redirect the received partially or wholly collimated light such that the redirected received partially or wholly collimated light has a third angular light distribution with a third angular centroid defining a third angular direction having a directional component extending towards the one or more second photodetectors to a greater extent than a corresponding directional component of the first angular direction.

18. The apparatus of claim 17, further comprising:
at least one or more additional photodetectors; and
at least one or more additional optical light field redirectors, wherein:
the one or more first photodetectors, the one or more second photodetectors, and the at least one or more additional photodetectors are located within an annular area centered on the collimating light source assembly, and
each of the one or more additional optical light field redirectors is positioned so as to receive at least some of the partially or wholly collimated light emitted by the collimating light source assembly and is configured to redirect the received partially or wholly collimated light such that the redirected received partially or wholly collimated light has an angular light distribution with an angular centroid defining an angular direction having a directional component extending towards a corresponding one of the at least one or more additional photodetectors to a greater extent than a corresponding directional component of the first angular direction.

19. The apparatus of claim 17, further comprising:
a first light barrier interposed between the collimating light source assembly and the one or more first photodetectors; and
a second light barrier interposed between the collimating light source assembly and the one or more second photodetectors.

20. An apparatus comprising:
a collimating light source assembly, the collimating light source assembly configured to emit partially or wholly collimated light having a first angular distribution with a first angular centroid defining a first angular direction, wherein the collimating light source assembly includes:
a plurality of light sources; and
a plurality of optical reflectors, wherein:
each optical reflector has a corresponding light source, and
the one or more optical reflectors are configured to reflect light from the corresponding light sources to generate the partially or wholly collimated light having the first angular distribution; and
one or more first photodetectors defining, in aggregate, a photosensitive surface, wherein the first angular direction is at an angle of between 5° and 50° with respect to a normal vector of the photosensitive surface and includes a directional component that is directed towards the first photodetector.

21. The apparatus of claim 20, further comprising a first light barrier interposed between the collimating light source assembly and the one or more first photodetectors.

22. The apparatus of claim 20, wherein the light sources are arranged in an array that is substantially parallel to the photosensitive surface.

23. The apparatus of claim 20, wherein the light sources are arranged in an array that is within 5° to 50° of parallel with the photosensitive surface.

24. The apparatus of claim 1, wherein the first optical light field redirector is offset from the collimating light source assembly by a first distance in a direction parallel to the first angular direction.

25. The apparatus of claim 1, wherein the first optical light field redirector is offset from the collimating light source assembly by a first distance defining a gap between the first optical light field redirector and the collimating light source assembly.

* * * * *